US012622648B2

(12) United States Patent
Pfeiffer et al.

(10) Patent No.: US 12,622,648 B2
(45) Date of Patent: May 12, 2026

(54) CONTROL DEVICE FOR CONTROLLING A MEASUREMENT SYSTEM FOR MEASURING BLOOD PRESSURE

(71) Applicant: KONINKLIJKE PHILIPS N.V., Eindhoven (NL)

(72) Inventors: Ulrich Joachim Pfeiffer, Boeblingen (DE); Benjamin Stolze, Taufkirchen (DE); Stephan Guido Maria Regh, Boeblingen (DE); Mahad Amer Akhter, Boeblingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 848 days.

(21) Appl. No.: 17/423,031

(22) PCT Filed: Jan. 9, 2020

(86) PCT No.: PCT/EP2020/050347
§ 371 (c)(1),
(2) Date: Jul. 14, 2021

(87) PCT Pub. No.: WO2020/148137
PCT Pub. Date: Jul. 23, 2020

(65) Prior Publication Data
US 2022/0096017 A1 Mar. 31, 2022

(30) Foreign Application Priority Data

Jan. 14, 2019 (EP) ..................................... 19151589
Nov. 11, 2019 (EP) ..................................... 19208237

(51) Int. Cl.
A61B 5/00 (2006.01)
A61B 5/022 (2006.01)
A61B 5/0225 (2006.01)

(52) U.S. Cl.
CPC .......... *A61B 5/725* (2013.01); *A61B 5/02225* (2013.01); *A61B 5/0225* (2013.01); *A61B 5/7278* (2013.01)

(58) Field of Classification Search
CPC ... A61B 5/725; A61B 5/02225; A61B 5/0225; A61B 5/7278
See application file for complete search history.

(56) References Cited

U.S. PATENT DOCUMENTS 5,759,157 A * 6/1998 Harada .............. A61B 5/02225
600/494
6,120,459 A 9/2000 Nitzan
(Continued)

FOREIGN PATENT DOCUMENTS

DE 102017110770 B3 * 8/2018 ............. A61B 5/022
EP 2759258 B1 9/2016
(Continued)

OTHER PUBLICATIONS

Bishop, S., et al. Multifractal Analysis of Hemodynamic Behavior: Intraoperative Instability and Its Pharmacological Manipulation [online]. Anesthesiology 2012. [retrieved on: May 9, 2024]. Retrieved from the internet. <URL: https://pubs.asahq.org/anesthesiology/ article/ 117/4/810/13344/Multifractal—(Year: 2012) Analysis-of-Hemodynamic> <DOI: https://doi.org/10.1097/ALN. 0b013e31826a4aa2> (Year: 2012).*
(Continued)

*Primary Examiner* — Alex M Valvis
*Assistant Examiner* — Jonathan M Haney
(74) *Attorney, Agent, or Firm* — Brynne J. Corcoran

(57) ABSTRACT
The invention relates to a control device for controlling a blood pressure measurement system. An applicator applies increasing pressure to a subject's part in a measurement time period, while the pressure (TP) on the skin of the subject's
(Continued)

part, which comprises a plurality of pressure pulses (9), is measured. For each pressure pulse of at least some of the plurality of pressure pulses, several features, which characterize the respective pressure pulse, are determined, wherein an end measurement time point (32), at or after which the measurement time period is to be stopped, is determined based on these features, and wherein, when or after the end measurement time point has been reached, i.e. when the measurement time period is to be stopped, the applied pressure is decreased to start the following post-blood-pressure-measurement time period. This allows for a reduced blood pressure measurement time and maximum tissue pressure exerted on the skin.

20 Claims, 12 Drawing Sheets

(56) References Cited

U.S. PATENT DOCUMENTS

| | | | |
|---|---|---|---|
| 8,430,822 | B2 | 4/2013 | Inoue |
| 8,864,678 | B2 | 10/2014 | Forstner |
| 11,406,272 | B2 | 8/2022 | Whitaker |
| 2010/0298726 | A1 | 11/2010 | Kim et al. |

| | | | | |
|---|---|---|---|---|
| 2015/0051500 | A1* | 2/2015 | Elliott | A61B 5/7405 |
| | | | | 600/491 |
| 2020/0077904 | A1* | 3/2020 | Kang | A61B 5/7239 |
| 2020/0288984 | A1* | 9/2020 | Ariyama | A61B 5/02141 |

FOREIGN PATENT DOCUMENTS

| | | | |
|---|---|---|---|
| EP | 3430992 | A1 | 1/2019 |
| JP | 2013236797 | A | 11/2013 |
| JP | 2018023624 | A | 2/2018 |
| WO | 2014121805 | A1 | 8/2014 |
| WO | 2014121945 | A1 | 8/2014 |
| WO | 2017169924 | A1 | 10/2017 |
| WO | 2018210931 | A1 | 11/2018 |

OTHER PUBLICATIONS

International Search Report and Written Opinion, International Application No. PCT/EP2020/050347, Mailed on Mar. 24, 2020.

Sasaki J, Kikuchi Y, Usuda T, Hori S. Validation of inflationary noninvasive blood pressure monitoring in the emergency room. Blood Pressure Monitoring. 2015;20(6):325-329. doi:10.1097/MBP. 0000000000000145.

"What is iNIBP?", Nihon Kohden, https://ae.nihonkohden.com/en/innovativetechnologies/inibp/what-is-inibp.html, Accessed Jul. 12, 2021.

* cited by examiner

CONTROL DEVICE FOR CONTROLLING A MEASUREMENT SYSTEM FOR MEASURING BLOOD PRESSURE

This application is the U.S. National Phase application under 35 U.S.C. § 371 of International Application No. PCT/EP2020/050347, filed on 9 Jan. 2020, which claims the benefit of European Application Serial No. 19151589.9, filed 14 Jan. 2019 and European Application Serial No. 19208237.8, field 11 Nov. 2019. These applications are hereby incorporated by reference herein.

FIELD OF THE INVENTION

The invention relates to a control device for controlling a measurement system for measuring blood pressure of a subject. The invention relates further to the measurement system for measuring blood pressure of the subject, and a control method and a computer program for controlling the measurement system.

BACKGROUND OF THE INVENTION

EP 3 430 992 A1 discloses a blood pressure measuring system configured to surround a subject's body part, wherein the blood pressure measuring system comprises pressurization means for applying pressure to the body part and a kinking-proof shell. The kinking-proof shell is arranged to be located between the pressurization means and the body part, when the blood pressure measuring system surrounds the body part. The blood pressure measuring system allows measuring the blood pressure very accurately by continuously raising clamping pressure and stopping the rise above systolic blood pressure, but it is desired to reduce the time needed for carrying out the blood pressure measurement and the maximum clamping pressure exerted on the body part during the measurement.

SUMMARY OF THE INVENTION

It is an object of the present invention to provide a control device for controlling a measurement system for measuring blood pressure of a subject, which allows for a reduced measurement time and for a reduced maximum clamping pressure exerted on the subject. It is a further object of the present invention to provide a measurement system for measuring blood pressure of a subject comprising the control device, and a control method and a computer program for controlling the measurement system.

In a first aspect of the invention a control device for controlling a measurement system for measuring blood pressure of a subject is presented, wherein the measurement system comprises a) a shell configured to encase a part of the subject, through which blood flows, b) a pressure applicator configured to apply, from outside the shell, pressure to the shell and thereby to the encased part of the subject, and c) a pressure sensor configured to measure the pressure on the skin of the encased part of the subject, wherein the control device is configured to control the measurement system such that the pressure applicator increases the applied pressure in a measurement time period and decreases the applied pressure in a following post-blood-pressure-measurement time period, the pressure sensor measures the pressure on the skin at least during the measurement time period, wherein the measured pressure comprises a plurality of pressure pulses, wherein the control device is configured to determine, for each pressure pulse of at least some of the plurality of pressure pulses, several features, which characterize the respective pressure pulse, to determine an end measurement time point, at which the measurement time period is to be stopped, based on the features determined for the at least some of the plurality of pressure pulses, and to control the pressure applicator such that, when or after the end measurement time point has been reached, it decreases the applied pressure to start the following post-blood-pressure-measurement time period.

It has been found that features determined for the pressure pulses can be used for determining an end measurement time point such that the measurement time period is relatively short and nevertheless enough pressure data have been measured, which allow for an accurate determination of the blood pressure. This allows for a reduced blood pressure measurement time and tissue pressure, i.e. the clamping pressure exerted on the skin of the body part, during measurement staying and ending substantially below systolic arterial pressure.

The features can directly characterize the respective pressure pulse or indirectly characterize the respective pressure pulse. In the latter case the respective pressure pulse is processed for determining a features determination pulse and the features are determined based on the determined features determination pulse. This will be explained in more detail further below. The control device can be configured to determine, for each pressure pulse of, for instance, at least 5 or at least 10 of the plurality of pressure pulses, several features, which characterize the respective pressure pulse. The control device can also be configured to determine, for each pressure pulse of the plurality of pressure pulses, several features which characterize the respective pressure pulse.

In an embodiment the pressure sensor, which is configured to measure the pressure on the skin of the encased part of the subject, is arranged inside the shell. However, the pressure sensor can also be arranged in another way for measuring the pressure on the skin of the encased part of the subject. For instance, a fluid filled pressure sensor pad can be arranged inside the shell and connected via a fluid path, i.e. via a fluid filled tubing, to a pressure sensor outside of the shell, in order to measure the pressure on the skin of the encased part of the subject.

Preferentially, the control device is configured to determine a) for a respective pressure pulse an end determination combination value by combining at least two of the features, which have been determined for the respective pressure pulse, such that for several pressure pulses, which are present at different times, several end determination combination values are determined, wherein the several end determination combination values determined for the several pressure pulses and hence for the several times form an end determination curve, and b) the end measurement time point based on the end determination curve. By using the end determination curve the accuracy of determining the end measurement time point can be further increased. The control device can be adapted to process the several end determination combination values, which are obtained for the several pressure pulses, for obtaining a continuous end determination curve. For obtaining the continuous curve based on the distinct end determination combination values known mathematical techniques can be used. For instance, an interpolation can be applied, a fitting procedure, a filtering procedure, et cetera.

It is further preferred that the control device is configured to, in order to determine for a respective pressure pulse several features, provide a features determination pulse based on the respective pressure pulse, and determine at least one of the following features a) the difference between the features determination pulse's maximum systolic pressure and the features determination pulse's pressure at the end-diastolic point, b) the duration of the respective features determination pulse, c) the area of the respective features determination pulse, and d) the width at half maximum of the respective features determination pulse. The difference between the maximum measured pressure and the minimum measured pressure of the respective pressure pulse preferentially corresponds to the difference between the tissue pressure, i.e. the measured pressure on the skin, of the respective pressure pulse at a maximum systolic point and the tissue pressure at an end diastolic point of the respective pressure pulse. The duration of the respective pressure pulse preferentially corresponds to the time difference between an end-diastolic point and the following end-diastolic point for the respective pressure pulse. Moreover, the area is preferentially the area under the curve of the respective features determination pulse from an end diastolic point to the following end diastolic point. The area can be a normalized area. For instance, the area can be normalized by scaling it to the difference between the maximum pressure and the minimum pressure of the respective features determination pulse. The width at half maximum corresponds to the width at 50 percent of the difference between the maximum pressure and the minimum pressure of the respective features determination pulse. Thus, it is the width at 50 percent of the difference between the pressure of the features determination pulse at the maximum systolic point and the pressure of the features determination pulse at an end diastolic point. It has been found that by using these features the determination of the end measurement time point can be further improved. The features determination pulse for a respective pressure pulse can be obtained, for instance, by subtracting a mean measured pressure from the respective pressure pulse. However, the features determination pulse for a respective pressure pulse can also be determined in another way. It can also directly be the respective pressure pulse, i.e. the respective measured pressure pulse.

In a preferred embodiment the control device is configured to determine an end determination combination value for a respective pressure pulse based on at least one of the following calculations i) multiplying a) the determined area to the power of a predetermined first exponent with b) the determined difference to the power of a predetermined second exponent, and ii) dividing a) the determined area to the power of a predetermined third exponent by b) the determined duration to the power of a predetermined fourth exponent and multiplying the resulting quotient with c) the determined difference to the power of a predetermined fifth exponent. It is also preferred that the control device is configured to determine an end determination combination value for a respective pressure pulse based on a further multiplication with the width at half maximum to the power of a further predetermined exponent. Thus, in an embodiment the above calculation i) and/or the above calculation ii) is extended by a multiplication with the width at half maximum to the power of a further predetermined exponent. The different exponents are preferentially predefined and can be predetermined by calibration measurements, wherein by invasive means reference blood pressure values are determined very accurately and the exponents are determined such that the measurement system controlled by the control device yields the very accurately invasively measured blood pressure values with high statistical precision and accuracy, whilst the blood pressure measurement time is substantially shorter than a conventional oscillometric noninvasive blood pressure measurement under the same conditions (e.g. height of blood pressure, of pulse pressure, and inversely of heart rate). In particular, for the calibration measurement pairs of simultaneously recorded invasive and noninvasive blood pressure values from an adequate number of individuals of all genders, of relevant ranges of body height, weight and ages in different hemodynamic conditions are used. It should be noted that the calibration is preferentially only carried out in a development phase, i.e. not during an actual blood measurement procedure. The calibration can be carried out separately for different shell sizes, i.e. preferentially for different blood pressure cuff sizes, or for different groups of shell sizes. For instance, for different shell sizes or groups of shell sizes, different sets of exponents can be determined by calibration, i.e. for each shell size or for each group of shell sizes a respective set of exponents can be determined.

The control device is preferentially further configured to determine a) for a respective pressure pulse a blood pressure determination combination value by combining at least two of the determined features such that for several pressure pulses, which are present at different times, several blood pressure determination combination values are determined, wherein the several blood pressure determination combination values determined for the several pressure pulses and hence for several times form a blood pressure determination curve, and b) the blood pressure based on the blood pressure determination curve. By using this blood pressure determination curve for determining the blood pressure, the blood pressure can be determined very accurately. Preferentially, the control device is configured to determine a maximum of the blood pressure determination curve and to determine the blood pressure based on the determined maximum and the measured pressure. Determining the blood pressure based on the determined maximum of the blood pressure determination curve and depending on the measured pressure on the skin, i.e. depending on the tissue pressure, allows to further increase the accuracy of determining the blood pressure.

The control device can be adapted to process the several blood pressure determination combination values, which are obtained for the several pressure pulses, for obtaining a continuous blood pressure determination curve. For instance, an interpolation can be applied and optionally also a smoothing.

Preferentially the control device is configured to determine a blood pressure determination combination value for a respective pressure pulse based on at least one of the following calculations i) multiplying a) the determined area to the power of a predetermined tenth exponent with b) the determined difference to the power of a predetermined eleventh exponent, and ii) dividing a) the determined area to the power of a predetermined twelfth exponent by b) the determined duration to the power of a predetermined thirteenth exponent and multiplying the resulting quotient with c) the determined difference to the power of a predetermined fourteenth exponent. It is further preferred that the control device is configured to determine a blood pressure determination combination value for a respective pressure pulse based on a further multiplication with the width at half maximum to the power of a further predetermined exponent.

Thus, in an embodiment the above calculation i) and/or the above calculation ii) is extended by a multiplication with the width at half maximum to the power of a further predetermined exponent. In addition, also these different exponents are preferentially predefined and can be predetermined by calibration measurements, wherein by invasive means reference blood pressure values are determined very accurately and the exponents are determined such that the measurement system controlled by the control device yields the very accurately invasively measured blood pressure values with high statistical precision and accuracy, whilst the blood pressure measurement time is substantially shorter than a conventional oscillometric noninvasive blood pressure measurement under the same conditions (e.g. height of blood pressure, of pulse pressure, and inversely of heart rate). In particular, for the calibration measurement pairs of simultaneously recorded invasive and noninvasive blood pressure values from an adequate number of individuals in different hemodynamic conditions are used. It should be noted again that the calibration is preferentially only carried out in a development phase, i.e. not during an actual blood measurement procedure. Also in this case the calibration can be carried out separately for different shell sizes, i.e. preferentially for different blood pressure cuff sizes, or for different groups of shell sizes. For instance, for different shell sizes or groups of shell sizes, different sets of exponents can be determined by calibration, i.e. for each shell size or for each group of shell sizes a respective set of exponents can be determined.

The control device is preferentially configured to determine the end determination curve such that it fulfills one of the following conditions a) a maximum of the end determination curve occurs temporally before a maximum of the blood pressure determination curve, b) a maximum of the end determination curve occurs temporally at or after a maximum of the blood pressure determination curve and the decrease of the end determination curve after its maximum is steeper than the decrease of the blood pressure determination curve after its maximum, and c) the end determination curve is identical to the blood pressure determination curve. It has been found that, if the end determination curve and the blood pressure determination curve have one of these relations with respect to each other, the end measurement time point can be even more accurately determined.

In a preferred embodiment, the control device is configured to determine the end measurement time point further based on the blood pressure determination curve. It has also been found that, if not only the end determination curve, but also the blood pressure determination curve, are used for determining the end measurement time point, the measurement time can be even further reduced.

Preferentially the control device is configured to determine the end measurement time point by determining when a) the end determination curve has fallen, after having passed its maximum, to a value being equal to or smaller than a predefined percentage of the maximum and b) the blood pressure determination curve has reached or passed its maximum. It is further preferred that the predefined percentage of the maximum is within a range from 40 percent to 95 percent. It has especially been found that, if both curves are used in this way for determining the end measurement time point, this time point can be determined very accurately such that the blood pressure measurement time is relatively short and blood pressure is nevertheless measured very precisely.

In an embodiment, the control device is configured to control the pressure applicator such that it increases the applied pressure with a first rate in a pre-measurement time period which is followed by the measurement time period in which the applied pressure is increased with a second rate, wherein the first rate is larger than the second rate. Thus, an applied pressure, at which the measurement time period should start, can be reached relatively fast, thereby allowing for a further reduction of the overall time needed for measuring the blood pressure.

In an embodiment the control device is configured to control the pressure applicator such that at the end of the pre-measurement time period the measured pressure is within the range of 15 to 30 mmHg. This ensures that during the measurement time period the pressure on the skin, i.e. the tissue pressure, is measured over a sufficiently large pressure range, which allows for an accurate and precise measurement of the blood pressure.

The range of 15 to 30 mmHg is preferentially applied, if a previous diastolic arterial pressure obtained by a previous blood pressure measurement of the same subject is not used by the control device for controlling the pressure applicator. If a previous diastolic arterial pressure is used for the control of the pressure applicator, the measured pressure at the end of the pre-measurement time period can also be higher. The control of the pressure applicator depending on a previously obtained diastolic arterial pressure will be explained below.

It should be noted that the pressure at the end of the pre-measurement time is not the pressure which is applied in between two subsequent blood pressure measurements, particularly before the pre-measurement time period starts. This pressure could be named "attachment pressure" and should not exceed 15 mmHg.

In an embodiment the control device is configured to a) store or receive a previous diastolic arterial pressure obtained by a previous blood pressure measurement, b) determine a first end measured pressure, which should be present at the end of the pre-measurement time period and which could therefore also be regarded as being a targeted pressure, depending on the previous diastolic arterial pressure, such that the first end measured pressure is smaller than the previous diastolic arterial pressure, and c) control the pressure applicator such that the measured pressure at the end of the pre-measurement time period is equal to or smaller than the determined first end measured pressure. It is preferred that the control device is configured to determine the first end measured pressure such that it is 90 percent or less of the previous diastolic arterial pressure. In addition, this ensures that during the measurement time period the pressure on the skin, i.e. the tissue pressure, is measured over a sufficiently large range to determine blood pressure accurately and precisely.

In an embodiment the control device is configured to further store or receive the time at which the previous diastolic arterial pressure had been measured and to determine the first end measured pressure depending on i) the previous diastolic arterial pressure and ii) a temporal distance to the blood pressure measurement, at which the previous diastolic arterial pressure had been measured, as indicated by the stored time. The diastolic arterial pressure can change with time, wherein the first end measured pressure can still be determined relatively accurately, if the temporal distance to the blood pressure measurement, at which the previous diastolic arterial pressure has been measured, is considered. Thus, although this uncertainty regarding the change of the diastolic arterial pressure over time is present, the end of the pre-measurement time period can be determined such that, during the following measurement time period, pressure on the skin, i.e. tissue pressure, is measured over a sufficiently large range to determine blood pressure accurately and precisely.

The control device can be further configured to a) store or receive a previous pressure measured by the pressure sensor in a time period in between an end of a previous measurement time period of a previous blood pressure measurement and a start of the pre-measurement time, and b) to control the pressure applicator such that the measured pressure at the start of the pre-measurement time period is equal to or smaller than a predefined pressure value based on the stored or received previous measure. The predefined pressure value is preferentially equal to or smaller than 15 mmHg, further preferred equal to or smaller than 10 mmHg.

The measured pressure at the start of the pre-measurement time period can be regarded as being the attachment pressure which is present during measurement pauses between two subsequent blood pressure measurements, i.e. before a respective blood pressure measurement starts, wherein this attachment pressure is preferentially controlled to achieve a given or pre-set value, i.e. the predefined pressure value. This control is preferentially carried out to adapt for changes in body part volume, e.g. increases caused by tissue edema (capillary leak like e.g. in sepsis, hypervolemia) or decreases by shrinking tissue edema or by hypovolemia. This should especially avoid venous congestion during measurement pauses, i.e. in between two subsequent blood pressure measurements, caused by compromised venous return by venous compression with tissue pressures higher than venous pressure in the respective body part. In a preferred embodiment the pressure on the skin, which can also be regarded as being tissue pressure, is continuously measured during the entire procedure of carrying out one or several blood pressure measurements and the pressure applicator is controlled such that venous congestion is avoided during measurement pauses.

In a further aspect of the present invention, a measurement system for measuring blood pressure of a subject is presented, wherein the measurement system comprises:

a shell configured to encase a part of the subject, through which blood flows, a pressure applicator configured to apply, from outside the shell, pressure to the shell and thereby to the encased part of the subject, a pressure sensor configured to measure the pressure on the skin of the encased part of the subject, and a control device as defined in any of claims 1 to 19.

In another aspect of the present invention a control method for controlling a measurement system as defined by claim 20 is presented, wherein the control method includes:

increasing the applied pressure in a measurement time period and decreasing the applied pressure in a following post-blood-pressure-measurement time period by using the pressure applicator, measuring the pressure on the skin at least during the measurement time period by using the pressure sensor arranged inside the shell, wherein the measured pressure comprises a plurality of pressure pulses, wherein, for each pressure pulse of at least some of the plurality of pressure pulses, several features, which characterize the respective pressure pulse, are determined and wherein an end measurement time point, at or after which the measurement time period is to be stopped, is determined based on the features determined for the at least some of the plurality of pressure pulses, and wherein the pressure applicator is controlled such that, when or after the end measurement time point has been reached, it decreases the applied pressure to start the following post-blood-pressure-measurement time period.

In a further aspect of the present invention a computer program for controlling a measurement system as defined by claim 19 is presented, the computer program comprising program code means for causing the measurement system to carry out the steps of claim 20, when the computer program is run on the control device of the measurement system.

The control device, method and computer program are preferentially adapted to continuously control the measurement system for carrying out several subsequent blood pressure measurements whilst attached to the subject.

It shall be understood that the claimed control device, measurement system, control method, and the computer program, have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
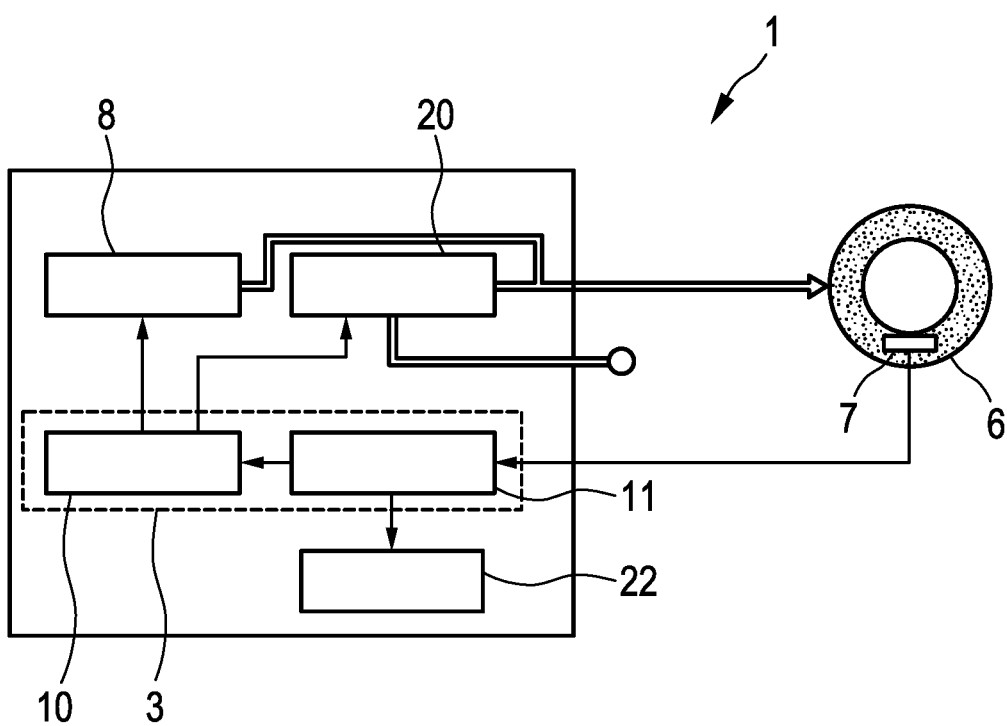
FIG. 1 shows schematically and exemplary an embodiment of a measurement system for measuring blood pressure of a subject in a situation in which a blood pressure cuff of the measurement system is inflated.
Figure 2:
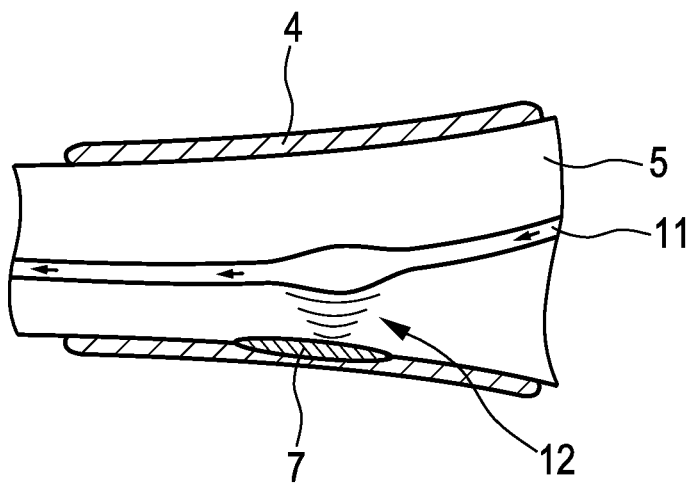
FIG. 2 shows schematically and exemplary a shell of the measurement system encasing an upper arm of the subject.

FIG. 1 shows schematically and exemplarily a measurement system 1 for measuring blood pressure of a subject. The measurement system 1 comprises a shell 4 which can be seen in FIG. 2 and which is configured to encase a part 5 of the subject, through which blood flows. In this embodiment the part 5 of the subject is an arm of the subject, wherein in FIG. 2 within the arm 5 a brachial artery 11 is shown and wherein the arrows within the brachial artery 11 indicate the flow direction of the blood away from the heart. The measurement system 1 further comprises a pressure sensor 7 arranged inside the shell 4 and configured to measure the pressure on the outer skin of the encased arm 5 of the subject. The measured pressure can also be regarded as being tissue pressure (TP). As indicated in FIG. 2, a pulse wave within the brachial artery 11 causes a pressure wave 12 which is transmitted to the pressure sensor 7 via the tissue of the arm 5. The shell 4 is not shown in FIG. 1 for clarity reasons.

The measurement system 1 further comprises cuff 6 which encloses the shell 4 and which is inflatable by using a pump 8 for applying, from outside the shell 4, pressure to the shell 4 and thereby to the encased arm 5 of the subject. Since the cuff 6 and pump 8 together enable an application of the pressure to the shell 4 and thereby to the encased arm 5 of the subject, they can be regarded as forming a pressure applicator 6, 8. The shell 4 with the cuff 6 is preferably a kinking-proof shell cuff as described in WO 2014/121945 A1.

The measurement system 1 further comprises a control device 3 being configured to control the measurement system 1 such that the pressure applicator 6, 8 increases the applied pressure in a measurement time period and decreases the applied pressure in a following post-blood-pressure-measurement time period and that the pressure sensor 7 measures the pressure on the skin, i.e. the tissue pressure TP at least during the measurement time period. Moreover, the control device 3 is configured to control the pressure applicator 6, 8 such that it increases the applied pressure with a first rate in a pre-measurement time period which is followed by the measurement time period in which the applied pressure is increased with a second rate, wherein the first rate is larger than the second rate. The control of the measurement system 1 such that the cuff 6 is inflated and hence the applied pressure is increased is illustrated in FIG. 1, i.e. the bold arrows indicate the inflation situation.

Figure 3:
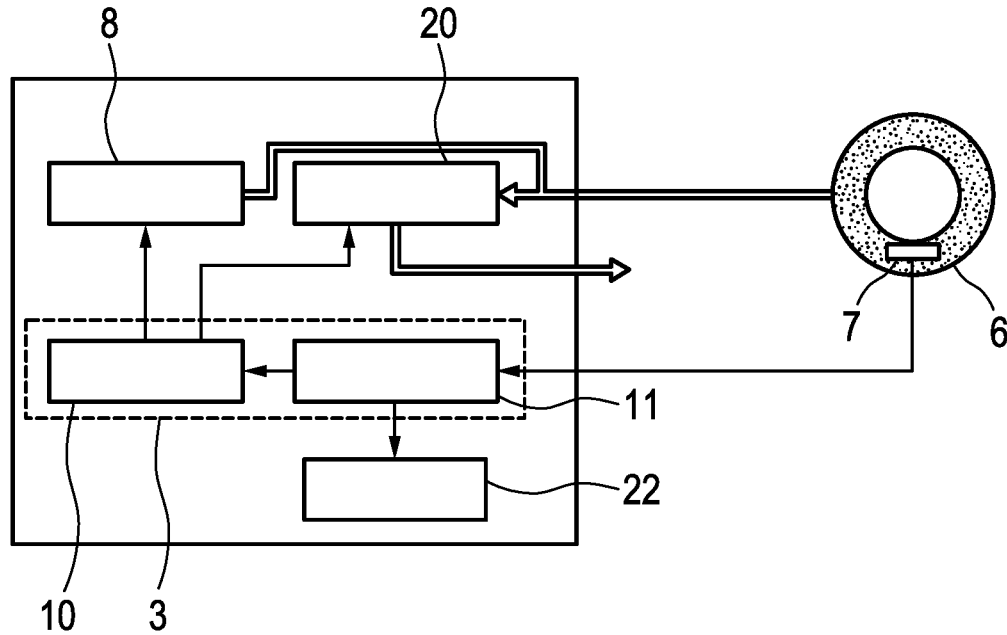
FIG. 3 shows schematically and exemplary the measurement system in a situation in which the blood pressure cuff is deflated.

The measurement system 1 comprises a valve 20 which, when the valve 20 is opened, allows the compressed air within the system to leave the system into the surrounding atmosphere for deflating the cuff. In FIG. 3 this deflation situation, in which the pump 8 is switched off, is indicated by the bold arrows.

The control device 3 can be regarded as comprising an actual controller 10 for controlling the pump 8 and the valve 20 and a processor 11, which especially is configured to carry out some calculations that will be explained further below. The measurement system 1 can also comprise a display 22 for displaying, for instance, a measured blood pressure value.

In the pre-measurement time period, which could also be regarded as being a fast inflation period, the control device 3 controls the measurement system 1 such that the valve 20 is closed and the pump 8 inflates the cuff 6 with the larger first rate. In the following measurement time period the control device 3 also controls the measurement system 1 such that the valve 20 is closed, but the pump 8 is controlled such that the inflation of the cuff 6 is continued with the lower second rate. The measurement time period could therefore also be regarded as being a slow inflation period.

Figure 4:
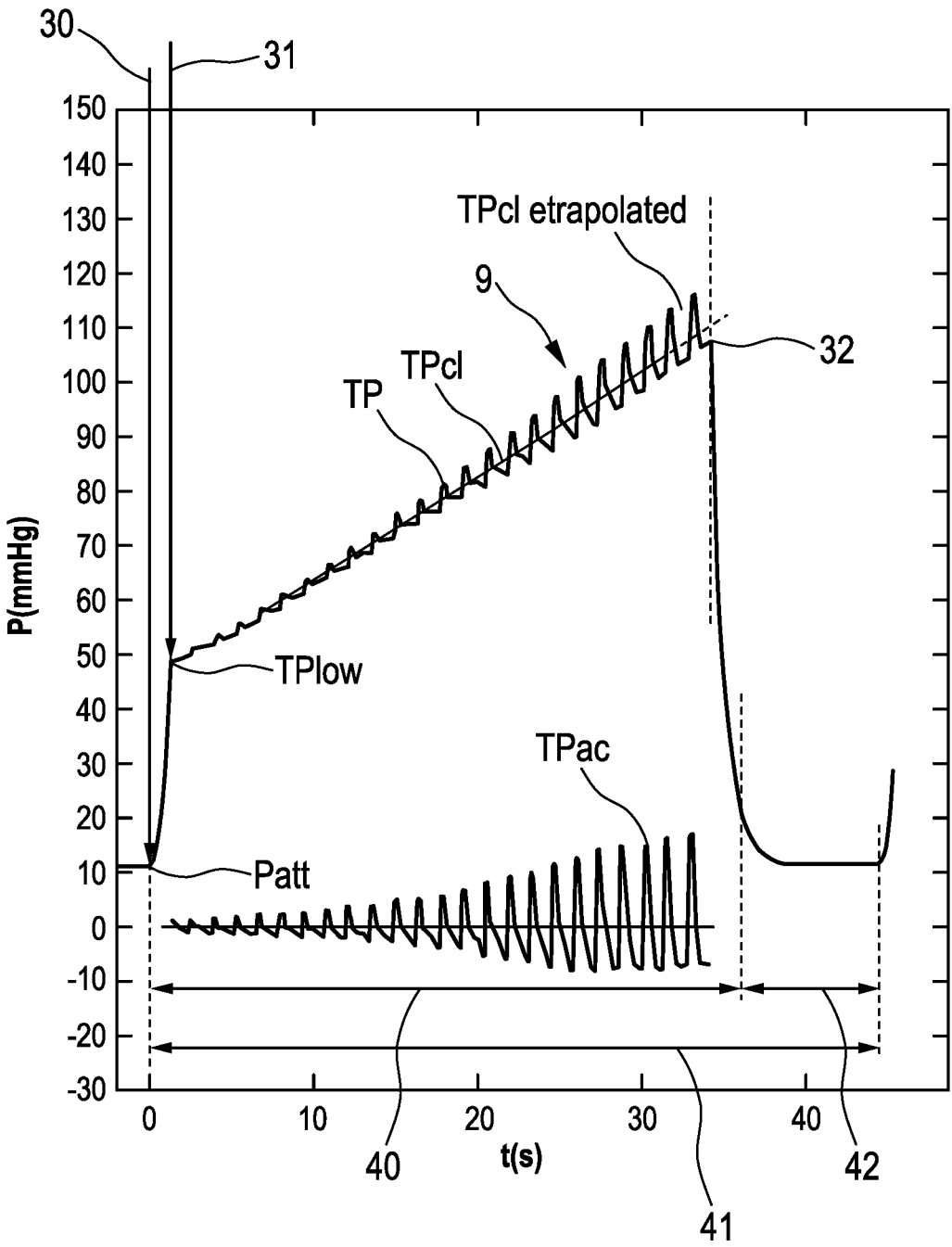
FIG. 4 shows schematically and exemplary a measured tissue pressure and further values derived from the tissue pressure measurement.

FIG. 4 schematically and exemplarily illustrates the measured pressure TP versus time t. The first inflation in the pre-measurement time period starts with a tissue pressure TP being an attachment pressure Patt that is the measured tissue pressure in the uninflated cuff 6. This attachment pressure Patt can range, for instance, from 0 to 15 mmHg. An attachment pressure Patt up to 15 mmHg has turned out to not result in venous congestion for more than 12 hours, thereby making the assembly of the shell 4 with the cuff 6 optimally suitable for longer term monitoring. For this reason, it is preferred that the attachment pressure Patt is not larger than 15 mmHg. In FIG. 4 the arrow 30 indicates the start of the pre-measurement time period, i.e. the start of the fast inflation period. During this pre-measurement time period the part of the overall tissue pressure range, which has no or substantially no information for the determination of the blood pressure, shall be passed as fast as possible. Therefore, the inflation rate is preferentially as large as possible during the pre-measurement time period. For instance, the inflation rate with respect to the tissue pressure TP can be equal to or larger than 8 mmHg/s. This pre-measurement time period with a fast inflation rate ends at a tissue pressure value which is indicated in FIG. 4 by "TPlow".

The tissue pressure value TPlow also indicates the start of the measurement time period with the slower second inflation rate. In FIG. 4 this start of the measurement time period, which can also be regarded as being a slow inflation period, is indicated by the arrow 31. In an embodiment, the control device 3 is configured to control the pump 8 such that at the end of the pre-measurement time period the measured pressure TPlow is within a range of 15 to 30 mmHg. Thus, in an embodiment the tissue pressure TPlow can be pre-defined such that it is a value between 15 and 30 mmHg. However, in a situation, in which a diastolic arterial pressure determined in a preceding measurement (DAPprev) is available, the tissue pressure TPlow can depend on this diastolic arterial pressure and the tissue pressure TPlow can also be larger. This larger TPlow is schematically shown in FIG. 4. For instance, the control device 3 can be configured to store (or access a memory storage with) a previous diastolic arterial pressure DAPprev. The previous diastolic arterial pressure DAPprev has been obtained by a previous blood pressure measurement and can be used to determine the tissue pressure TPlow. The tissue pressure TPlow should be present at the end of the pre-measurement time period, i.e. of the first inflation period, and could therefore also be regarded as being a first end measured pressure. The tissue pressure TPlow is determined depending on the previous diastolic arterial pressure DAPprev such that the tissue pressure TPlow is smaller than the previous diastolic arterial pressure DAPprev. Preferentially, the control device is configured to control the pump 8 such that the measured pressure at the end of the pre-measurement time period is equal to the determined first end measured pressure TPlow. In an embodiment the control device 3, particularly the processor 11 of the control device 3, determines the tissue pressure TPlow at the end of the pre-measurement time period such that it is not above a predetermined percentage of the previous diastolic arterial pressure DAPprev. This can ensure that all necessary tissue pressure pulse curves, which allow for an accurate calculation of the blood pressure, are recorded. The calculation of the blood pressure based on the measured tissue pressure will be explained further below. The predetermined percentage is preferentially 90 percent.

The blood pressure can change between measurements due to, for instance, clinically relevant events occurring to the subject. It has been found that the diastolic arterial pressure (DAP) might decrease by about 30% within one minute in most severe situations of acute blood loss during surgery. In order to cope with these possible blood pressure changes, the control device 3 can be adapted to determine the tissue pressure TPlow depending on the previous diastolic arterial pressure DAPprev and depending on duration of a break time between measurements. Thus, the control device 3 can be configured to further store (or access the memory storage with) the time at which the previous diastolic arterial pressure DAPprev had been measured and to determine the first end measured pressure TPlow depending on i) the previous diastolic arterial pressure DAPprev and ii) a temporal distance to the blood pressure measurement, at which the previous diastolic arterial pressure DAPprev had been measured as indicated by the stored time. An exemplary specific equation for determining the first end measured pressure TPlow will be given further below.

The second inflation rate applied during the measurement time period is preferentially within a range from 1 mmHg/s to 6 mmHg/s, the lowest inflation rate preferentially at 1.5 mmHg/s, the highest preferentially 2.5 mmHg/s. It has been found that a second inflation rate within this range allows for an accurate blood pressure determination. It should be noted that these rates refer to the changes of the tissue pressure TP as measured by the pressure sensor 7.

In an embodiment the slower second inflation rate depends on the heart rate (HR) and/or the pulse pressure (PP) being the difference between the systolic and diastolic blood pressure. For instance, the second inflation rate can increase with increasing heart rate and with increasing pulse pressure PP. This increase can be linear or can be described by another functional relation. In an embodiment this functional relation is such that at a heart rate HR of 40/min and at a pulse pressure PP of 20 mmHg the tissue pressure inflation rate is 1 mmHg/s and at a heart rate of HR of 80/min and at a pulse pressure PP of 100 mmHg the tissue pressure inflation rate, i.e. the second slow inflation rate, is 10 mmHg/s. The measurement time period ends at an end measurement time point 32, thereafter an immediate fast deflation follows preferentially with a maximally possible decrease rate, because no tissue pressure data needs to be collected after the end measurement time point 32. The measured pressure TP comprises a plurality of pressure pulses 9, wherein the control device 3 is configured to determine, for each pressure pulse of at least some of the plurality of pressure pulses 9, several features, which characterize the respective pressure pulse, to determine the end measurement time point 32, at or after which the measurement time period is to be stopped, based on the features determined for the plurality of pressure pulses 9, and to control the pressure applicator 6, 8 such that, when or after the end measurement time point 32 has been reached, it decreases the applied pressure to start the following post-blood-pressure-measurement time period being the time period at which the fast deflation is carried out.

In FIG. 4 the time interval 40 indicates the inflation-deflation time period from the start 30 of fast inflation until the tissue pressure TP has dropped below 20 mmHg during the fast deflation, in order to allow venous return. The time period 41 indicates a cycle time being the time between a start of a measurement and a start of a following measurement and the time period 42 indicates a break period being the difference between the inflation-deflation time period 40 and the cycle time 41.

FIG. 4 also illustrates mean pressure TPcl that can be regarded as being a tissue clamping pressure affecting the tissue when the cuff 6 is attached to the arm 5, for instance, to the upper arm, of the subject. The mean pressure TPcl can be calculated by applying a low pass filter to the tissue pressure TP, wherein the low pass filter might be located within the control device 3, particularly in the processor 11 of the control device 3. The low pass filter is preferentially dimensioned such that the mean pressure TPcl comprises frequencies below the lowest expected pulse rate (PRni) only. Preferred low pass filters will be described further below. The control device 3 is preferentially configured to determine an alternating component TPac of the tissue pressure by subtracting the mean pressure TPcl from the measured tissue pressure TP, i.e. TPac=TP−TPcl. In FIG. 4 the TPac curve is shown enlarged by a factor of 2, in order to improve visibility of this curve.

During the slow inflation period, i.e. during the measurement time period, TP pulse curves and/or TPac pulse curves are recorded, which may be analyzed and parameters calculated simultaneously, i.e. on-line, wherein the TP pulse curves and/or the TPac pulse curves have tissue pressure waveforms (TPW) comprising information which allows for an accurate determination of the blood pressure. Since the blood pressure is noninvasively measured (although it nevertheless has an accuracy which is comparable to the accuracy of invasively measured blood pressure), it can be abbreviated with niBP meaning "noninvasive blood pressure". A TPac pulse curve is schematically and exemplarily shown in FIGS. 5 to 7.

Figure 5:
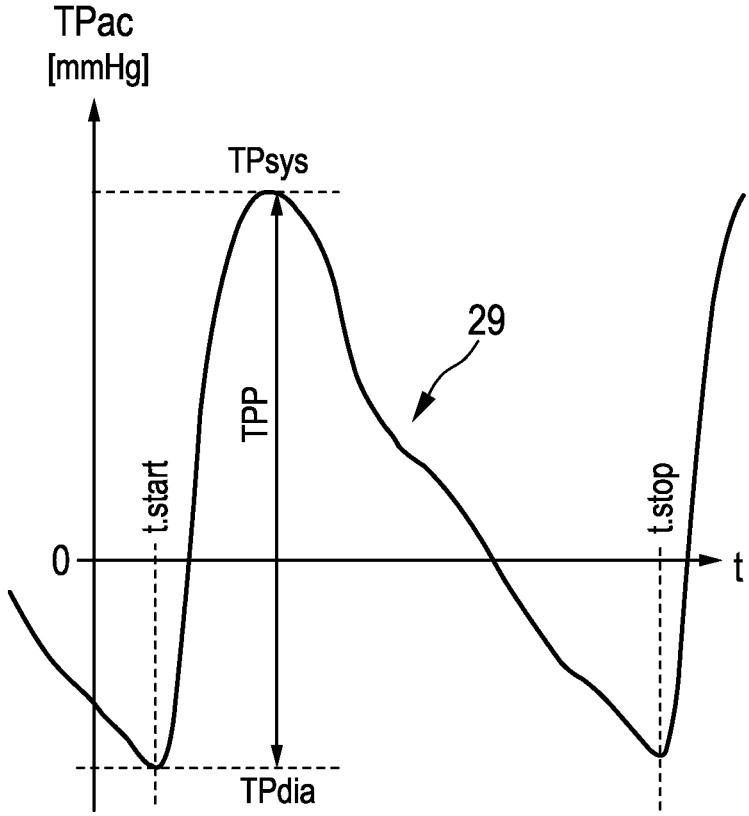
FIG. 5 illustrates a calculation of a first feature for a pressure pulse of the measured tissue pressure.
Figure 6:
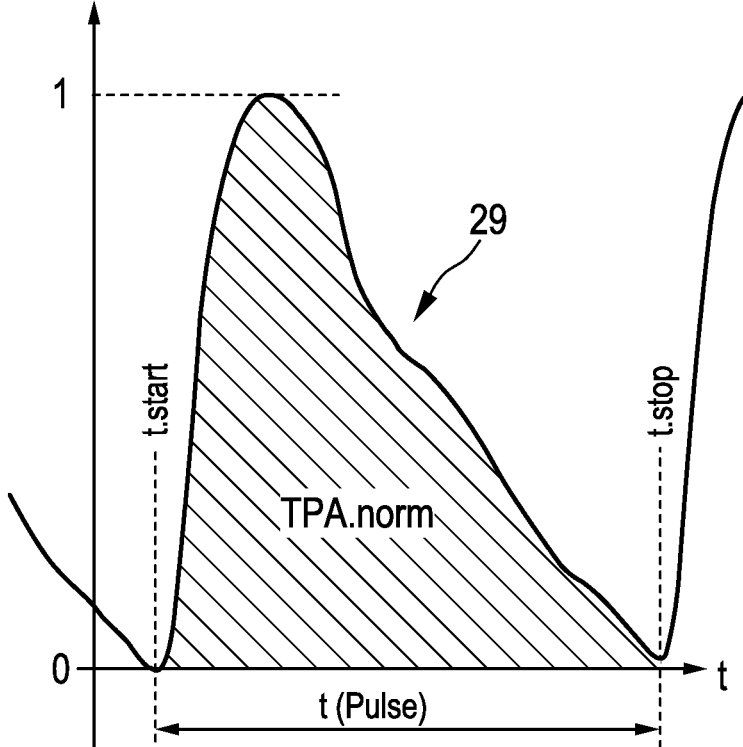
FIG. 6 illustrates a calculation of further features for the pressure pulse of the measured tissue pressure.
Figure 7:
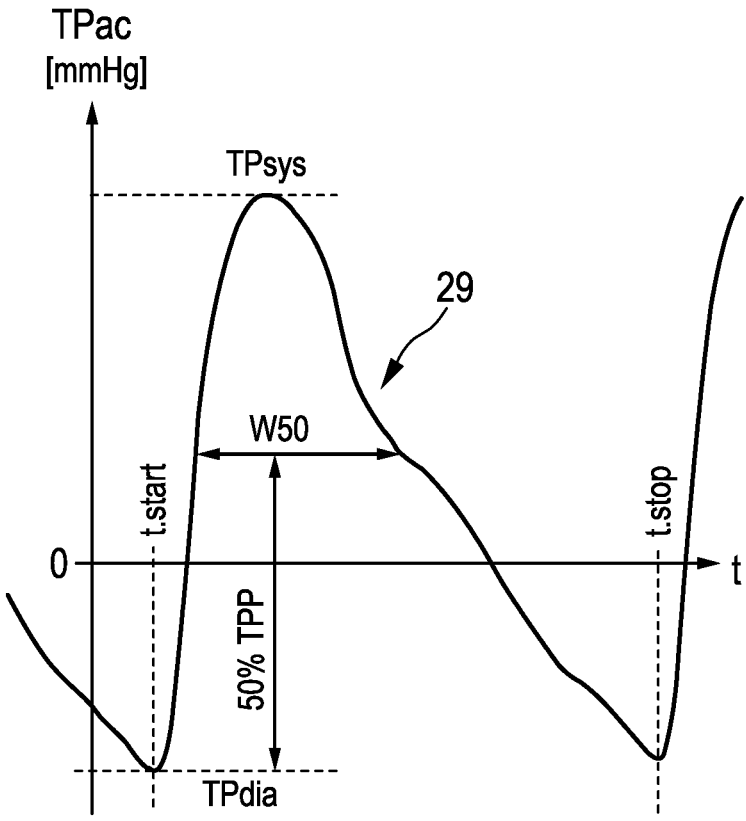
FIG. 7 illustrates a calculation of a further feature for the pressure pulse of the measured tissue pressure.

In the following the TPac pulse curves are used for determining features for the pressure pulses 9. The TPac pulse curves can therefore be regarded as being features determination pulse curves or features determination pulses. FIGS. 5 to 7 hence show features determination pulse curves or features determination pulses 29 being TPac pulses. In another embodiment the features determination pulses can also directly be the TP pulse curves, i.e. the pressure pulses 9 can be directly used for determining the features.

The control device 3 is configured to determine for a respective pressure pulse of the plurality of pressure pulses 9 several features which characterize the respective pressure pulse and to determine the end measurement time point 32, at or after which the measurement time period is stopped, based on the features determined for the plurality of pressure pulses 9. The determination of several features for a respective pressure pulse, which might also be regarded as being TPW parameters, will be described in the following.

It has been observed that, when increasing the clamping pressure, i.e. when increasing the pressure applied to the arm 5 via the cuff 6, the diastolic tissue pressure pulse form changes from a rather pointed shape to a flattened diastolic shape when crossing the mean arterial pressure (MAP) as can be seen in FIG. 7A, 7B, 7C of WO 2018/210931 A1. This behavior can be modelled by the changes of several TPW parameters. TPW parameters can be extracted from the TP pulse curves as described in this document WO 2018/210931 A1.

In an embodiment, the control device 3 is configured to determine a TPP difference between a maximum measured pressure and a minimum measured pressure of the respective features determination pulse 29 as a feature for the respective pressure pulse. This feature, i.e. this TPW parameter, will be described with reference to FIG. 5 in the following.

The difference TPP is a difference of a features determination pulse's maximum systolic pressure TPsys and the features determination pulse's pressure at an end-diastolic point (TPdia), which is preferably the minimum pressure of the respective features determination pulse. In FIG. 5 and also in FIGS. 6 and 7 the terms "t.start" and "t.stop" indicate the start and the end, respectively, of the respective pulse 29.

The control device 3 can also be configured to determine the pulse duration (t(Pulse)) being the time difference between an end-diastolic point and a following end-diastolic point of the features determination pulse 29. This feature can also be defined as being the temporal difference between the start of the respective pulse (t.start) and the end of the respective pulse (t.stop). This feature is indicated in FIG. 6.

The control device 3 can also be adapted to determine the pulse area (TPA) of the respective pulse 29 being the area under the respective pulse curve within the time defined by t.start to t.stop and ranging from the features determination pulse's pressure at an end-diastolic point (TPdia) to a features determination pulse's maximum systolic pressure (TPsys). Preferentially, the pulse area TPA is scaled to TPP=1 as indicated in FIG. 6. This scaled pressure pulse area is named "TPA.norm".

The control device 3 can also be adapted to determine the pulse width at half maximum (W50) of the respective pulse 29 as indicated in FIG. 7.

FIGS. 5 to 7 show a TPac pulse curve such that in this example also the features, i.e. the TPW parameters, have been defined based on the TPac pulse curve. However, as mentioned above, it is also possible to define these or other features based on a TP pulse curve.

The control device 3 is further configured to determine, for each pressure pulse, an end determination combination value TPWP_E, which could also be named "pulsation power parameter", by combining at least two of the features which have been determined for the respective pressure pulse. In particular, the control device 3 can be configured to multiply a) the determined pulse area TPA.norm to the power of a predetermined first exponent (exp1) with b) the determined difference TPP to the power of a predetermined second exponent (exp2). Thus, an end determination combination value TPWP_E can be calculated in accordance with following equation:

$$TPWP\_E=TPA.\text{norm}^{exp1}\cdot TPP^{exp2} \qquad (1)$$

with predetermined exp1≠0, exp2≠0.

The control device 3 can also be configured to determine an end determination combination value TPWP_E by dividing a) the determined pulse area TPA.norm to the power of a predetermined third exponent (exp3) by b) the determined pulse duration t(pulse) to the power of a predetermined fourth exponent (exp4) and multiplying the resulting quotient with c) the determined difference TPP to the power of a predetermined fifth exponent (exp5). This can be expressed by following equation:

$$TPWP\_E=TPA.\text{norm}^{exp3}/t(\text{Pulse})^{exp4}\cdot TPP_{exp5} \qquad (2)$$

with predetermined exp3≠0, exp4≠0, exp5≠0.

The control device 3 can also be configured to determine an end determination combination value for a respective pressure pulse based on multiplying the calculation result as obtained by using, for instance, equation (1) or equation (2), with the width at half maximum (W50) to the power of a further predetermined exponent. For instance, if equation (2) is multiplied by the width at half-maximum W50, the following equation (3) results:

$$TPWP\_E=TPA.\text{norm}^{exp6}/t(\text{Pulse})^{exp7}\cdot TPP^{exp8}\cdot W50^{exp9} \qquad (3)$$

with predetermined exp6≠0, exp7≠0, exp8≠0, exp9≠0.

Thus, in this embodiment based on at least TPP and TPA.norm for a respective pulse curve a TPWP_E can be calculated that reflects a characteristic value for the respective pulse curve by combining and weighting the amplitude and area parameters, wherein any of the TPWP_E can be extended by multiplying with W50 to the power of a respective exponent. The exponents for the different equations are predetermined, preferentially in the way that will be explained further below.

After for each pressure pulse a respective end determination combination value TPWP_E has been determined by combining at least two of the features, which have been determined for the respective pressure pulse, for several pressure pulses and hence for different times several end determination combination values TPWP_E are available, i.e. a curve TPW_E-curve can be obtained, which can be named "end determination curve", because the control device 3 is configured to determine the end measurement time point 32 based on this curve TPW_E-curve.

The control device 3 is further configured to determine for a respective pressure pulse a blood pressure determination combination value TPWP_M by combing at least two of the determined features such that for several pressure pulses, which are present at different times, several blood pressure determination combination values TPWP_M are determined, wherein the several blood pressure determination combination values TPWP_M determined for the several pressure pulses and hence for several times form a blood pressure determination curve TPW_M-curve. The control device 3, particularly the processor 11 of the control device 3, is configured to determine the blood pressure based on the blood pressure determination curve TPW_M-curve. In an embodiment the blood pressure determination curve TPW_M-curve is determined as explained in WO 2018/210931 A1. Particularly determining the arterial blood pressure based on the determined maximum of the blood pressure determination curve and depending on the exerted pressure on the skin, i.e. tissue pressure, allows a relatively short measurement time. Generally, the tissue pressure is dependent on the height of arterial blood pressure, of arterial pulse pressure, and the inverse of the heart rate.

The control device 3 can be configured to determine a blood pressure determination combination value TPWP_M for a respective pressure pulse based on multiplying a) the determined area TPA or TPA.norm to the power of a predetermined tenth exponent (exp10) with b) the determined difference TPP to the power of a predetermined eleventh exponent (exp11). For instance, for the respective pressure pulse a blood pressure determination combination value TPWP_M can be calculated in accordance with following equation:

$$TPWP\_M=TPA.\text{norm}^{exp10}\cdot TPP^{exp11} \qquad (4)$$

with predetermined exp10≠0, exp11≠0.

The control device 3 can also be configured to determine a blood pressure determination combination value TPWP_M for a respective pressure pulse by dividing a) the determined area TPA or TPA.norm to the power of a predetermined twelfth exponent (exp12) by b) the determined duration (t(Pulse)) to the power of a predetermined thirteenth exponent (exp13) and multiplying the resulting quotient with c) the determined difference TPP to the power of a predetermined fourteenth exponent (exp14). For instance, a blood pressure determination combination value TPWP_M can be calculated in accordance with following equation:

$$TPWP\_M=TPA.\text{norm}^{exp12}/t(\text{Pulse})^{exp13}\cdot TPP^{exp14} \qquad (5)$$

with predetermined exp12≠0, exp13≠0, exp14≠0.

The control device 3 can also be configured to determine a blood pressure determination combination value TPWP_M for a respective pressure pulse by further multiplying with the width at half-maximum W50 to the power of a further predetermined exponent. For instance, a blood pressure determination combination value TPWP_M can be calculated in accordance with following equation $$TPWP\_M=TPA.\mathrm{norm}^{exp15}/t$$
$$(\mathrm{Pulse})^{exp16} \cdot TPP^{exp17} \cdot W50^{exp18} \qquad (6)$$

with predetermined $exp15 \neq 0$, $exp16 \neq 0$, $exp17 \neq 0$, $exp18 \neq 0$.

The control device 3 is preferentially configured to determine the end determination curve TPW_E-curve such that it fulfills one of the following conditions a) a maximum of the end determination curve (TPW_E-curve.max) occurs temporally before the maximum of the blood pressure determination curve (TPW_M-curve.max), b) a maximum of the end determination curve (TPW_E-curve.max) occurs temporally at or after a maximum of the blood pressure determination curve (TPW_M-curve.max) and the decrease of the end determination curve TPW_E-curve after its maximum is steeper than the decrease of the blood pressure determination curve TPW_M-curve after its maximum, and c) the end determination curve TPW_E-curve is identical to the blood pressure determination curve TPW_M-curve. Thus, the exponents are preferentially predefined such that a) TPW_E-curve.max occurs temporally before TPW_M-curve.max or b) TPW_E-curve.max occurs at the time of TPW_M-curve.max or temporally after, but TPW_E-curve has a negative derivative with a larger absolute derivative value than the absolute derivative value of the negative derivative of the blood pressure determination curve TPW_M-curve after its maximum or c) TPW_E-curve can be identical to TPW_M-curve, i.e. the end determination curve and the blood pressure determination curve can be identical.

Figure 8:
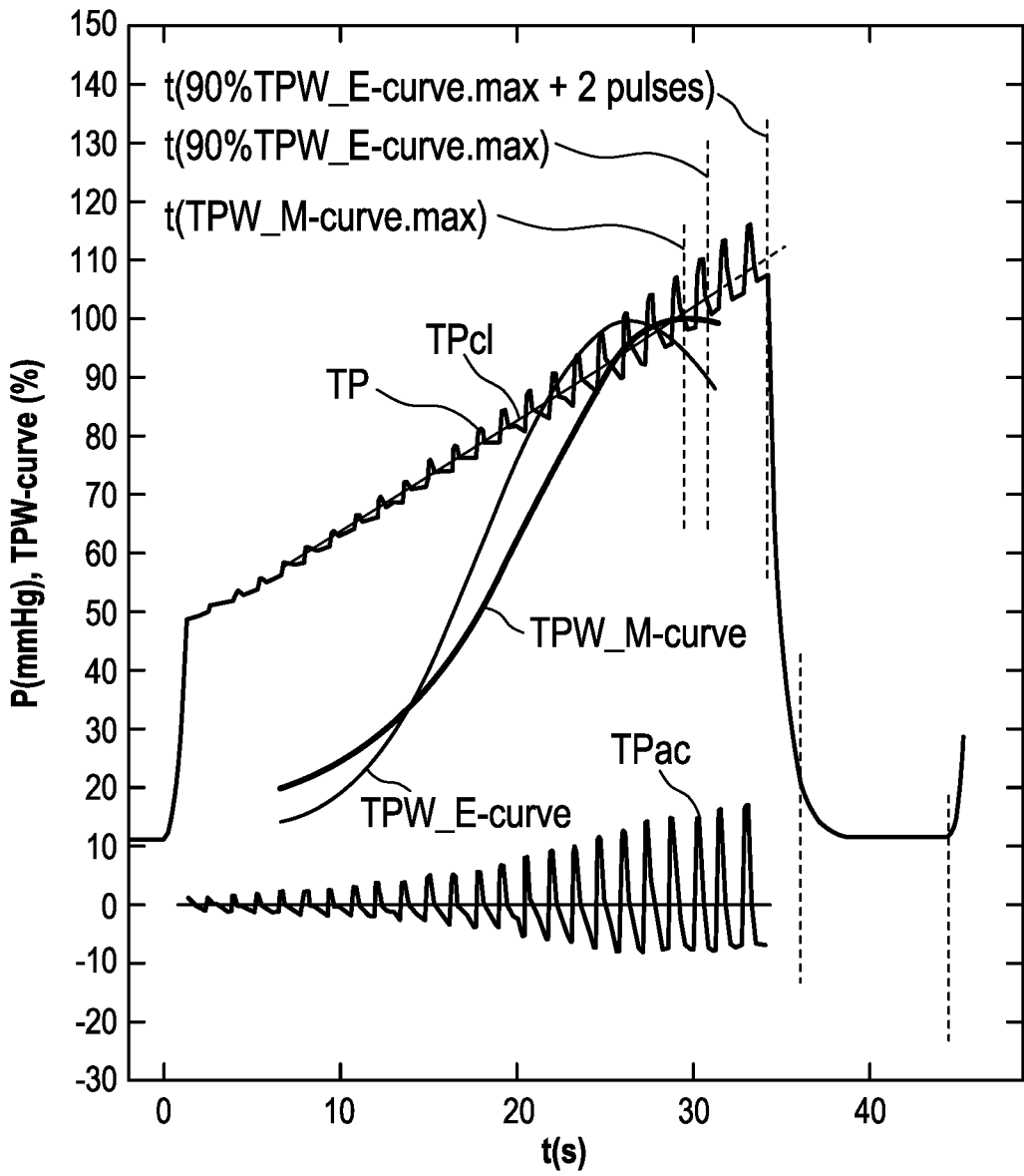
FIG. 8 shows schematically and exemplary an end determination curve and a blood pressure determination curve.

In FIG. 8 a blood pressure determination curve TPW_M-curve and an end determination curve TPW_E-curve are exemplarily shown, wherein these curves have been normalized such that the respective maximum corresponds to 100 percent.

It is desirable to terminate each blood pressure measurement as soon as possible to minimize stress for the subject, i.e. for the subject. The blood pressure measurement can be terminated as soon as the maximum of the blood pressure determination curve TPW_M-curve has been formed and hence can be completely determined, because the maximum of the blood pressure determination curve TPW_M-curve is used for the noninvasive blood pressure determination. Thus, during the measurement time period it is checked when an end criterion is reached, which defines the end measurement time point, wherein for determining when this end criterion is reached and hence for determining the end measurement time point preferentially the end determination curve TPW_E-curve and the blood pressure determination curve TPW_M-curve are used. For instance, when the end determination curve TPW_E-curve has formed its maximum, it can be checked with each newly measured TP pulse curve, i.e. with each newly measured TP pulse, if a) the end determination curve TPW_E-curve has decreased below a percentage of the maximum of the end determination curve TPW_E-curve, wherein this percentage is preferentially within a range from 40 percent to 95 percent, and b) the blood pressure determination curve TPW_M-curve has formed its maximum, i.e. has reached or passed its maximum. The control device 3 can be configured to determine the end measurement time point 32 as the time point at which both conditions a) and b) are met.

In order to determine whether the blood pressure determination curve TPW_M-curve has reached or passed its maximum safely, it can be detected whether the blood pressure determination curve TPW_M-curve has fallen after its maximum. In an embodiment the blood pressure determination curve TPW_M-curve can be a smoothed curve such that the maximum of the blood pressure determination curve is also smoothed. The smoothing procedure used for smoothing the blood pressure determination curve can include, for instance, filtering and/or fitting. Further, several pressure pulses can be considered, after the smoothed maximum, to detect the smoothed maximum unambiguously wherein the number of these several pulses can be predetermined or can depend on the heart rate of the subject. For instance, this number can increase with increasing heart rate. In an embodiment this number is 3 for a heart rate of 60/min and 10 for a heart rate of 200/min.

For smoothing the blood pressure determination curve TPW_M-curve a moving average filter, particularly a variable moving average filter, can be used that is applied on at least the several pressure pulses. The window used for the averaging can be fixed or variable, wherein in the latter case it preferentially has a maximum duration of, for instance, 8 s. The use of this filter causes a filter delay, wherein the minimum filter delay is as long as the added up durations of the several pulses. Having a filter delay with a length of the several pulses suffices to safely determine a falling smoothed blood pressure determination curve TPW_M-curve and therefore a maximum in the blood pressure determination curve TPW_M-curve. That means as soon as a decrease in the smoothed blood pressure determination TPW_M-curve is detected, the measurement time period will be terminated without needing to collect more pressure pulses. This is possible because of the, in this example, smoothing of the blood pressure determination curve TPW_M-curve with relatively large variable moving average filtering windows of, for instance, at least three TP pressure pulses and maximal 8 s, and applying the moving average filtering twice (2×8 s filter), that removes disturbing heart-lung interaction in estimated 95 percent of measurements. These smoothing filter windows can be made adaptive to the respiratory rate respectively ventilation rate, thereby allowing to improve the elimination of unwanted TPW_M-curve disturbances caused by heart-lung interaction.

In FIG. 8 both conditions a) and b) are met, when the end determination curve TPW_E-curve has decreased below 90 percent of the maximum of the end determination curve TPW_E-curve. Due to the filter delay the measurement is terminated a few tissue pressure pulses after both and conditions a) and b) have been met.

The continuous TPW_E-curve and the continuous TPW_M-curve shown in FIG. 8 have been obtained by filtering the values TPWP_E and TPWP_M, respectively, which had been determined for the different pressure pulses. This filtering, which leads to the filter delay, will be explained further below. In FIG. 8 the filter delay results in two additional pressure pulses such that the fast deflation of the cuff 6 starts two pressure pulses after both conditions a) and b) had been met.

An end determination curve TPW_E-curve having a maximum temporally occurring before the maximum of the blood pressure determination curve TPW_M-curve by some seconds allows for a shortening of the measurement time period, i.e. allows for a shortening of the slow inflation time and reduced amount of pressure applied to the subject. After reaching t(a_end), i.e. after reaching the time point at which the end determination curve TPW_E-curve has decreased below a predefined percentage of the maximum of the TPW_E-curve, the largest maximum of the blood pressure determination curve TPW_M-curve found so far, if the TPW_M-curve has several maxima, is the absolute maximum of the blood pressure determination curve TPW_M-curve (TPW_M-curve.max), if the blood pressure determination curve TPW_M-curve is decreasing at the time t(a_end). Otherwise, in an embodiment, a measurement will be continued until the next maximum of the TPW_M-curve and the maximum of the blood pressure determination curve (TPW_M-curve.max) will be determined afterwards.

Without using the end determination curve TPW_E-curve with a maximum temporally occurring before the maximum of the blood pressure determination curve TPW_M-curve, the slow inflation would need to continue until the blood pressure determination curve TPW_M-curve has fallen below a certain percentage of its maximum. In average by using the end determination curve TPW_E-curve with a maximum occurring temporally before the maximum of the blood pressure determination curve TPW_M-curve, a blood pressure measurement can be terminated after about 20 to 60 seconds at a TPcl within a range of 70 to 95 percent of systolic arterial pressure (SAP). This is significantly below the end pressure level of a conventional oscillometric niBP measurement. There the blood pressure measurement is terminated when the clamping pressure has reached about SAP+20 mmHg. When using the measurement system 1 as described above with reference to FIG. 1 and when the measurement is terminated, the tissue pressure TP drops as fast as possible to Patt remaining there for some time, preferably for about 20 percent of the inflation-deflation time period 40 indicated in FIG. 4, before another measurement is started.

The control device 3, particularly the processor 11 of the control device 3, is configured to determine the blood pressure based on the blood pressure determination curve TPW_M-curve, especially based on the maximum of the blood pressure determination curve TPW_M-curve. The control device 3 can be adapted to perform this determination of the blood pressure, which is a noninvasive blood pressure, as described in WO 2018/210931 A1.

Figure 9:
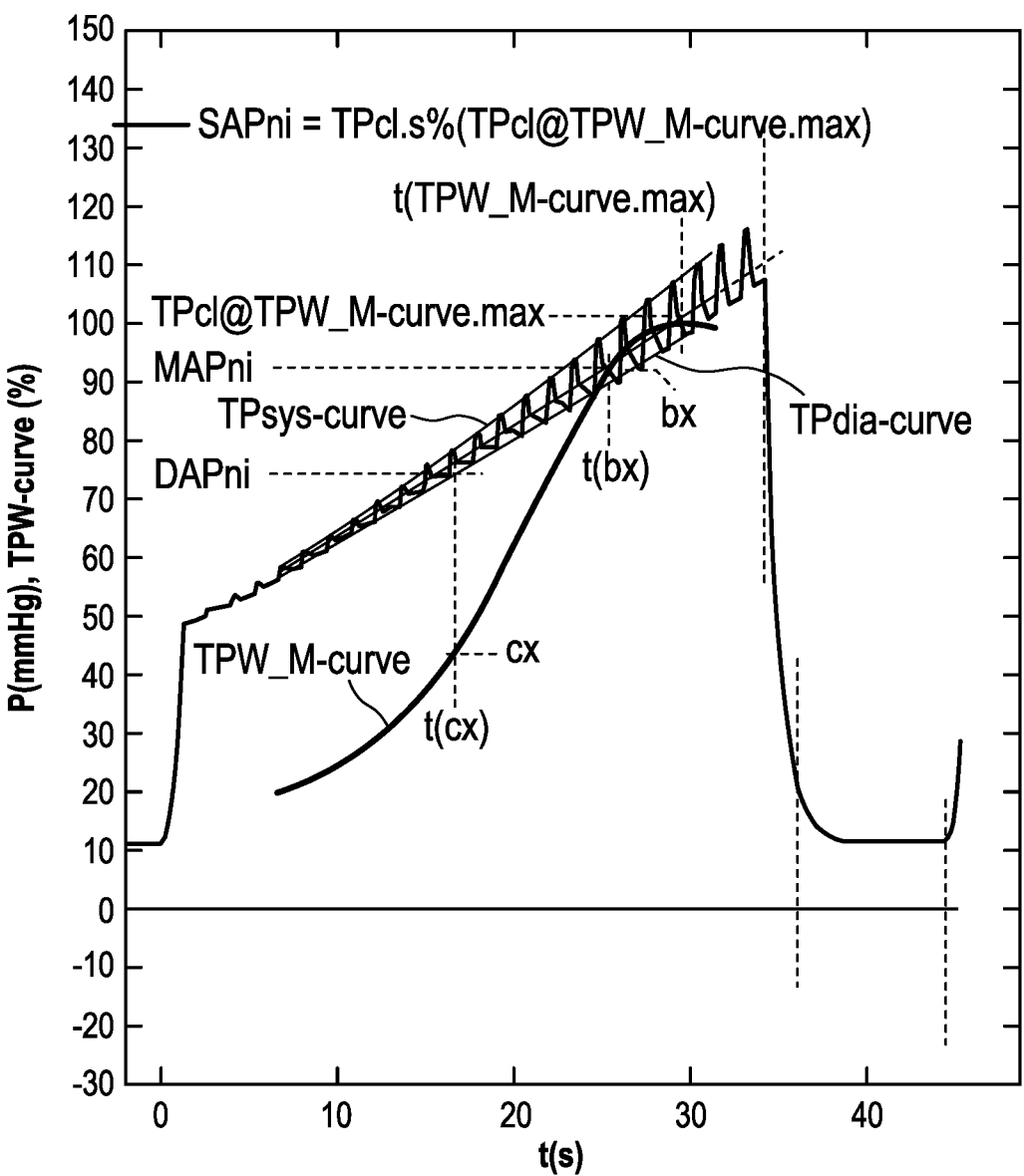
FIG. 9 illustrates schematically and exemplary a determination of blood pressure values by using the blood pressure determination curve.

In an embodiment the control device 3 is configured to determine the TPcl value at the time point at which the blood pressure determination curve TPW_M-curve has its maximum (TPW_M-curve.max), wherein in FIG. 9 the TPcl value at the time of this maximum is denoted as "TPcl@TPW_M-curve.max". The control device 3 is further configured to determine a lower envelope of the tissue pressure TP by applying a filter to the end-diastolic points of the tissue pressure TP. The filter can be same as the filter used for determining, for instance, the blood pressure determination curve TPW_M-curve. The resulting curve is named "TPdia-curve" in FIG. 9. Moreover, the control device 3 can be configured to determine an upper envelope of the tissue pressure TP by applying a filter to the systolic maxima of the tissue pressure TP. In addition, this filter can be similar to the filter used for, for instance, generating the blood pressure determination curve TPW_M-curve. This curve is named "TPsys-curve" in FIG. 9.

The control device 3 can then be configured to determine the systolic arterial pressure value as a predetermined percentage (TPcl.s %) of TPcl@TPW_M-curve.max. This predetermined percentage is preferentially within a range from 100 to 150 percent, further preferred from 110 to 150 percent. In FIG. 9 the noninvasive systolic arterial pressure is named "SAPni" and the predetermined percentage is denoted as "TPcl.s % (TPcl@TPW_M-curve.max)". In FIG. 9 the noninvasive systolic arterial pressure SAPni is about 134 mmHg.

The control device 3 can also be adapted to determine the noninvasive systolic arterial pressure SAPni as a predetermined percentage (TPsys.s %) of the TPsys curve at the temporal position at which the blood pressure determination curve TPW_M-curve has its maximum. This predetermined percentage is preferentially within a range from 100 to 140 percent.

The control device 3 can be configured to determine the noninvasive mean arterial pressure (MAPni) as the TPcl value or alternatively the value of the TPdia-curve or alternatively the value of the TPsys-curve at a time point t(bx) being the time point at which the blood pressure determination curve TPW_M-curve has a value bx representing a predetermined percentage relative to its maximum. The control device 3 can also be adapted to alternatively determine the noninvasive mean arterial pressure MAPni as a predetermined percentage (TPcl.m %) of TPcl at TPW_M-curve.max, wherein the predetermined percentage is preferentially within a range from 80 to 110 percent.

The control device 3 can also be configured to determine the noninvasive diastolic arterial pressure DAPni as the value of the TPdia-curve or alternatively of the TPcl curve at a time point t(cx) being the time point at which the blood pressure determination curve TPW_M-curve has a value cx representing a predetermined percentage of its maximum. The control device 3 can also be configured to alternatively determine DAPni as a predefined percentage (TPcl.d %) of TPcl@TPW_M-curve.max, wherein this predetermined percentage is preferentially within a range from 60 to 80 percent.

As explained above, the exponents used for determining the end determination curve TPW_E-curve and for determining the blood pressure determination curve TPW_M-curve are determined by calibration. Also the percentages used for determining the blood pressure values are determined by calibration. Thus, these parameters are predetermined such that, during a calibration phase, deviations between very accurately measured invasive blood pressure values and the blood pressure values obtained by the measurement system are minimized and the time needed for a blood pressure measurement is relatively low. Preferentially, thereby the set of exponents used for determining the blood pressure determination curve TPW_M-curve, which might be regarded as being a first set of exponents, is chosen in a way to achieve a good balance between high accuracy noninvasive blood pressure on one hand and a low TP level at the end of the measurement and therefore a low measurement time on the other hand. If the exponents were chosen such that they create a TPW_M-curve with a relatively early maximum, the TP level at the end of the measurement and the measurement time would be relatively low. However, the accuracy and position of the finally determined noninvasive blood pressure values is then also reduced. Thus, the first set of exponents is preferentially chosen such that a desired balance between measurement time and accuracy of the noninvasive blood pressure values is achieved.

The exponents used for determining the end determination curve TPW_E-curve, which might be regarded as forming a second set of exponents, is preferentially chosen such that the maximum of the end determination curve TPW_E-curve is relatively early. In an embodiment the first set of exponents and the second set of exponents can also be the same such that the end determination curve TPW_E-curve and the blood pressure determination curve TPW_M-curve can also be the same.

The values TPcl.s %, TPsys.s %, TPcl.m %, TPcl.d %, bx, cx are preferentially calibrated as described in WO 2018/

210931 A1 by statistically evaluation of a calibration set consisting of measurement pairs of simultaneously recorded invasive blood pressure values and noninvasive blood pressure values from an adequate number of individuals in different hemodynamic conditions. The noninvasive blood pressure values are determined as described above by the measurement system 1 and the parameters like the values TPcl.s %, TPsys.s %, TPcl.m %, TPcl.d % can be optimized such that deviations between invasive blood pressure values and noninvasive blood pressure values are minimized.

The control device 3, particularly the processor 11 of the control device 3, can be adapted to estimate a kind of blood pressure value based on two other already measured kinds of blood pressure values. In particular, one of the blood pressure values MAPni, SAPni and DAPni can be estimated based on the other of these blood pressure values. This may be done in accordance with following equations:

$$SAPni=c1 \cdot MAPni+c2 \cdot (MAPni-DAPni)-c3 \text{ mmHg} \quad (7)$$

with c1=(0.2 . . . 0.7), c2=(2 . . . 6), c3=(−5 . . . 5), $$MAPni=c4 \cdot DAPni+c5 \cdot (SAPni-DAPni)-c6 \text{ mmHg} \quad (8)$$

with c4=(0.8 . . . 1.3), c5=(0.25 . . . 0.5), c6=(−5 . . . 5), $$DAPni=c7 \cdot MAPni-c8 \cdot (SAPni-MAPni)-c9 \text{ mmHg} \quad (9)$$

with c7=(0.6 . . . 1.1), c8=(0.15 . . . 0.4), c9=(−5 . . . 5). The coefficients and constants of equations (7), (8) and (9) are predetermined by calibration based on a statistical evaluation of an as large as possible and adequately widely spread set of clinical invasive blood pressure data. Thus, very accurate invasive blood pressure values SAPi (invasive systolic arterial pressure), MAPi (invasive mean arterial pressure) and DAPi (invasive diastolic arterial pressure) are used, wherein, given these very accurate invasive blood pressure values, the coefficients and constants of the equations (7), (8) and (9) are modified such that these equations are valid.

The blood pressure measurement is intended to be used in a sequence of measurements in rapid succession to allow for an effective semi-continuous blood pressure monitoring such that the stress for the monitored individual, i.e. for the monitored subject, is minimized. This sequence of fast pressure measurements can also be regarded as being a noninvasive fast mode cycle (FMC) measurement of the blood pressure.

Figure 10:
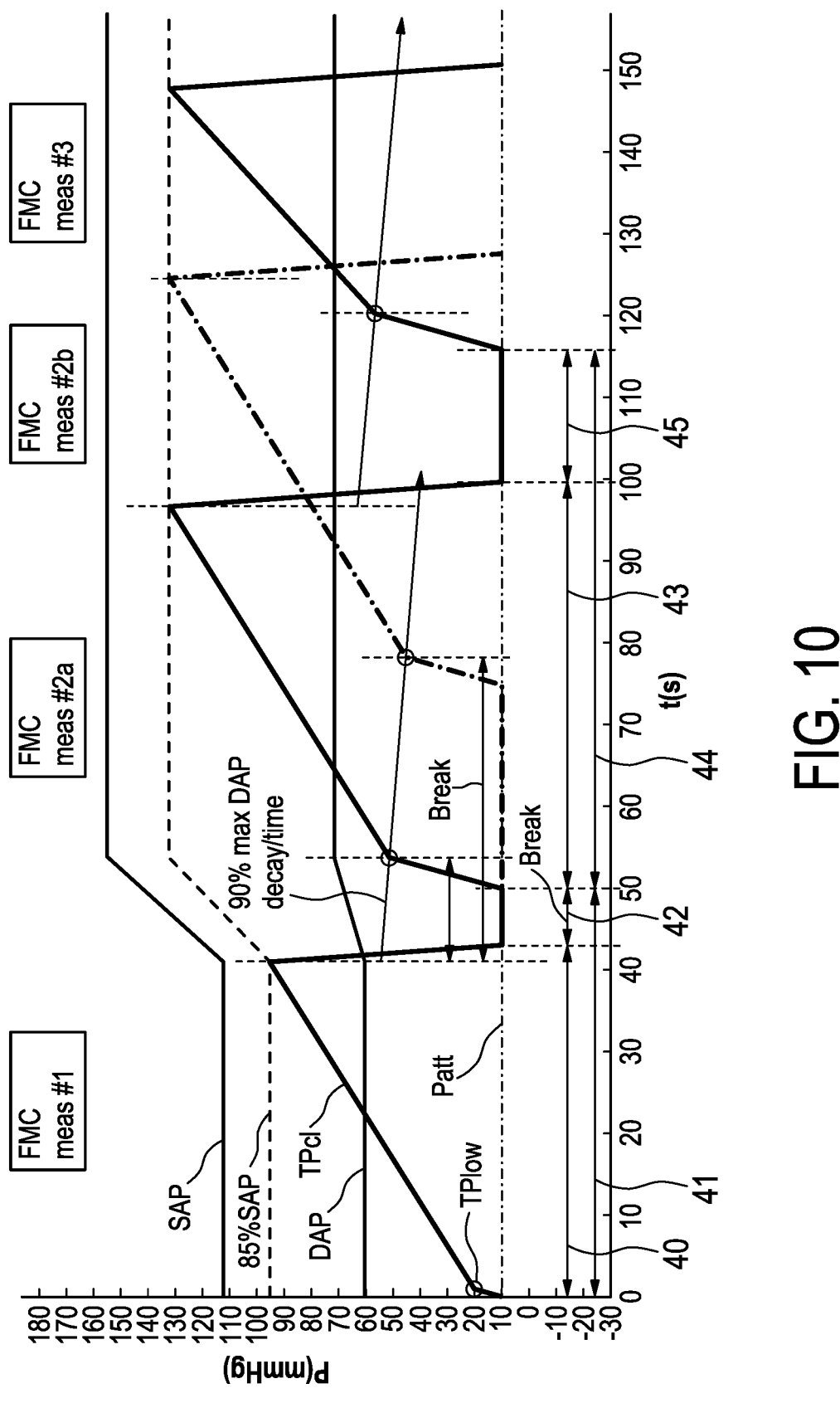
FIG. 10 shows schematically and exemplary an example of several successive blood pressure measurements.

In an embodiment the initial blood pressure measurement has no information about a previous diastolic arterial pressure (DAP) and is therefore starting the slow inflation, i.e. the measurement time period, at a predetermined tissue pressure TPlow within a range from 15 to 30 mmHg. Moreover, in this measurement time period the inflation rate is set to a medium value. The inflation rate can be defined as the rate with which TPcl increases over time, wherein this inflation rate can be chosen such that it has a value of, for instance, 1.9 mmHg/s. This would correspond to measurement of "normal" blood pressure values. At the end of the deflation phase, when TPcl has reached Patt, the blood pressure measurement preferentially has a break of at least 2 s, in order to allow reperfusion of the body part of the subject encased by the shell 4. This break time 42 has preferentially a length within a range from more than 0 to about 50 percent of the preceding inflation-deflation time period 40 resulting in cycle 41. The following blood pressure measurements will use the information of the diastolic arterial pressure (DAP) determined in the respective preceding measurement (DAPprev) to start the slow inflation, i.e. the measurement time period, with a higher TPlow as shown in FIG. 10.

The TPlow value should not be above 90 percent of the diastolic arterial pressure to ensure that all pulses necessary for the calculations of blood pressure are recorded. Furthermore, as explained above, the blood pressure can change in time intervals (t_inter) between a start of deflation and a start of a next slow inflation. Hence, preferentially a function to model the blood pressure decrease depending on the time intervals t_inter is applied. It has been observed in clinical data from high-risk surgery that the diastolic arterial pressure can decrease by more than 28 percent within one minute. Thus, TPlow could be calculated by using a linear function like the following function:

$$TPlow=90\% \ DAPprev-28\% \ DAPprev \cdot t\_inter/60 \text{ s}, \quad (10)$$

wherein "90% DAPprev" and "28% DAPprev" denote 90 percent and 28 percent, respectively, of the previously measured diastolic arterial pressure DAPprev.

TPlow can be determined by using a linear function, which depends on the previous time interval between the start of deflation and the start of the next slow inflation, wherein the linear function has a negative slope such that TPlow decreases with time. The slope of the linear function and also the positive constant of the linear function can be predetermined by calibration. In equation (10) the positive constant is 90% DAPprev and the negative slope is −28% DAPprev. The positive constant and the negative slope could also have other values. For instance, the negative slope could be −30% DAPprev.

In FIG. 10 it can be seen how TPlow is adapted depending on t_inter in accordance with equation (10). It can especially be seen that the measurements #2a and #2b have different TPlow values, wherein the TPlow value for the measurement #2b is smaller than the TPlow value for the measurement #2a, because for the measurement #2b the time interval t_inter is larger than for the measurement #2a. In FIG. 10 it can also be seen that the inflation rate for the measurement #3 is increased due to an increase of PP before the measurement #2a. Moreover, for the measurement #3 TPlow is larger in comparison to the previous measurements, because the diastolic arterial pressure DAP has increased before the measurement #2a. It should be noted that in FIG. 10 the interval 44 is the cycle period for the second measurement #2a, the interval 43 is the inflation-deflation period for the second measurement #2a and the interval 45 is the break time for the second measurement #2a. Moreover, it should be noted that the third measurement #3 refers to the second measurement #2a and that the further second measurement #2b is just shown for illustrating an alternative to the second measurement #2a.

Figure 11:
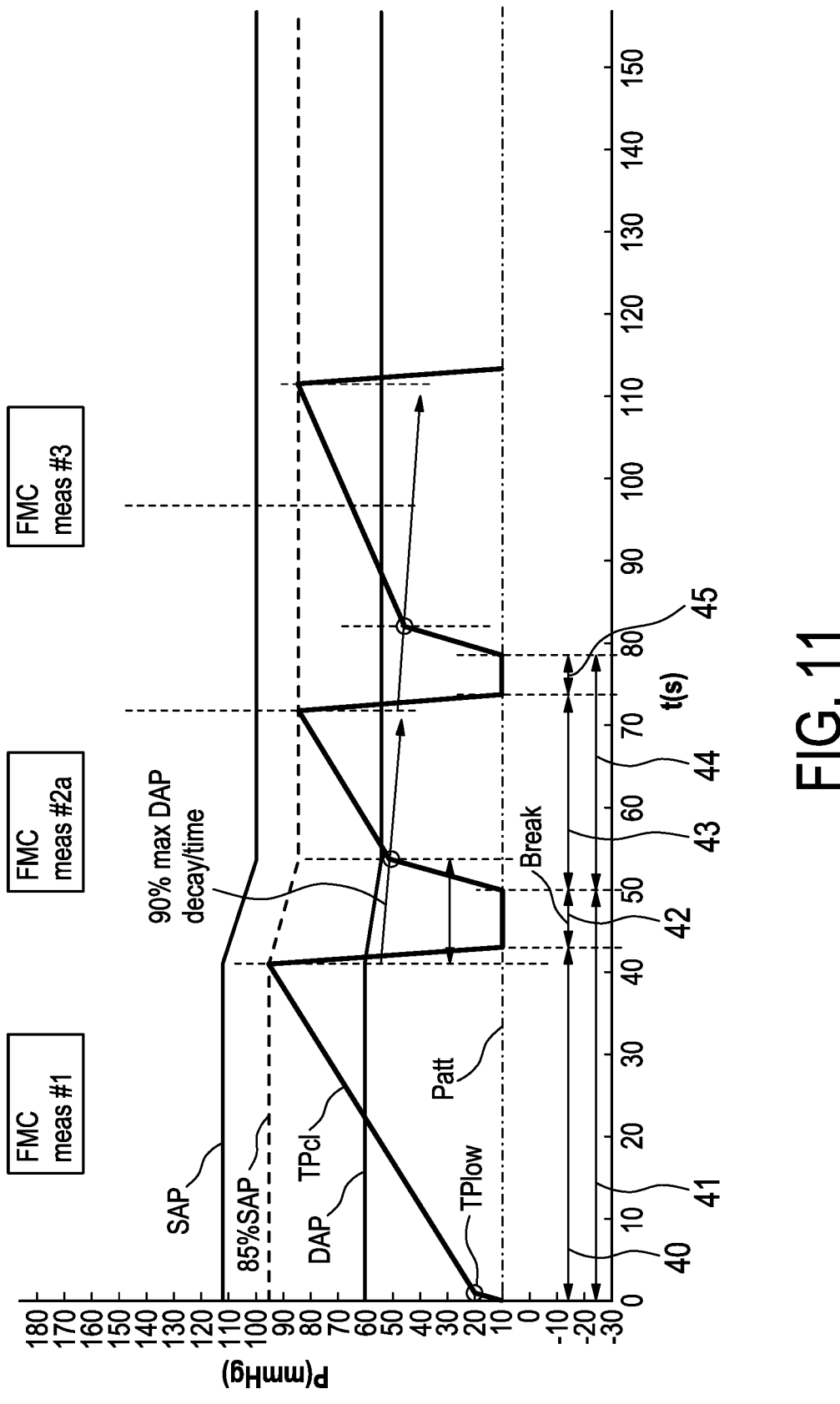
FIG. 11 shows schematically and exemplary a further example of several successive blood pressure measurements.

FIG. 11 shows a further example for adapting the TPlow value depending on the time interval t_inter in accordance with the equation (10). In this example the inflation rate in the measurement time period is decreased for the measurement #3 in comparison to the previous measurement due to a PP decrease before the measurement #2a and a lower TPlow value due to a decrease of DAP before the measurement #2a.

As explained above, for determining the end determination curve TPW_E-curve, the blood pressure determination curve TPW_M-curve and the envelope curves TPsys-curve and TPdia-curve a filter is used. Moreover, also for determining TPcl based on TP a filter is used. As the filter preferentially a low pass filter is used. The low pass filter can be, for instance, a cascaded moving average filter with a varying window length of up to 8 s, wherein the window length can be shorter at the beginning and at the end of the filtering, in order to a minimize filter settling time. For instance, the filtering can include averaging within a moving window containing signals of at least three TP pressure pulse curves and maximal 8 s, and applying the moving average filtering twice (2×8 s filter). Optionally, a signal padding can be applied before the beginning and/or after the end of the signal for fully filling the filter windows before filtering. For instance, padding with the first pressure pulse's value before the beginning and the last pressure pulse's value after the end can be applied.

Due to the filter delay TPcl is extrapolated from its previous values to be available for the last part of the measured signal. The filter can be applied to, for instance, extract TPcl from TP, form a smooth TPW_E-curve and a smooth TPW_M-curve without variation caused by blood pressure pulsation and to create an envelope function over systolic peaks (TPsys-curve) and over end-diastolic minima (TPdia-curve) of TP.

In a preferred embodiment, for defining the blood pressure determination curve TPW_M-curve, equation (5) is used with following exponents exp12=0.7, exp13=0.4 and exp14=1.0. By using these exponents together with equation (5) for inflation-deflation time periods within a range from 20 to 60 seconds a very good precision and accuracy could be obtained for the blood pressure values as validated with statistical evaluation of noninvasive blood pressure values as determined by the measurement system 1 versus simultaneously taken invasive blood pressure reference values. The following set of exponents together with equation (4) leads to an even higher precision and accuracy, but leads also to a few seconds longer measurement time: exp10=1.0, exp11=1.21.

In an embodiment, for determining the end determination curve TPW_E-curve, equation (2) is used together with following exponents: exp3=1.1, exp4=0.4, exp5=0.5. It has been found that, by using these exponents, a relatively early end of the slow inflation period, i.e. a relatively early end measurement time point, with an inflation-deflation time period within a range from 20 to 60 s can be determined.

Figure 12:
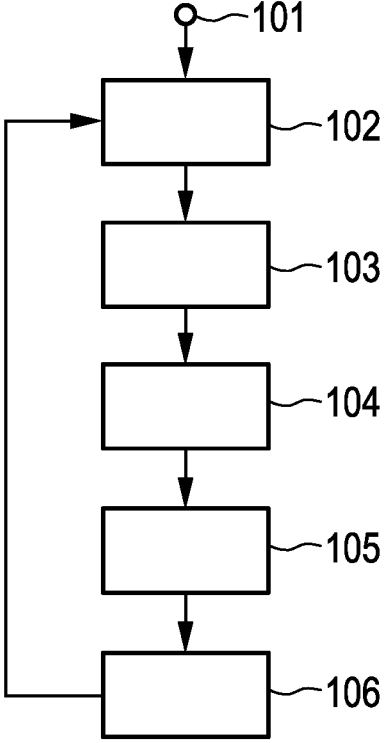
FIG. 12 shows a flowchart exemplary illustrating an embodiment of a control method for controlling the measurement system for measuring blood pressure of a subject.

In the following an embodiment of a control method for controlling the measurement system 1 will be exemplary described with reference with to a flowchart shown in FIG. 12.

After initializing and starting the system in step 101, in step 102 TPlow is determined. For a first measurement it can be a value from 15 mmHg to 30 mmHg. If blood pressure measurements have already been carried out, a previous diastolic arterial blood pressure value could be used, for instance in accordance with equation (10), for determining TPlow.

In step 103 in the pre-measurement time period the cuff is inflated with a relatively large first inflation rate until TPlow has been reached. Then, in step 104 the measurement time period, i.e. the slow inflation period, starts, wherein during this measurement time period the blood pressure determination curve TPW_M-curve and the end determination curve TPW_E-curve are determined. Moreover, these curves are used for determining an end measurement time point, wherein, when this end measurement time point has been reached or passed, the slow inflation period is stopped and in step 105 the cuff is deflated. After deflation and a pause for allowing venous return in step 106, the method continues with step 102. Thus, the control method can be carried out in a loop for continuously monitoring the blood pressure over time in several measurement cycles. While carrying out steps 102 to 105, the control device calculates the blood pressure value in parallel. The loop can be carried out until an abort criterion is fulfilled. For instance, the monitoring of the blood pressure is interrupted, if a physician has inputted a corresponding command into the measurement system via an input unit like a keyboard, a computer mouse, a touchpad, et cetera.

The measurement system allows for a noninvasive FMC measurement of blood pressure based on noninvasive high-fidelity tissue pressure TP recordings preferably recorded with a kinking-proof shell system as described in WO 2014/121945 A1. The measurement system preferentially allows for a statistical mean maximum pressure inflation of about 85 percent of the systolic arterial pressure or less. A single blood pressure measurement by using the measurement system 1 generally takes about 20 to 60 s depending on the height of arterial blood pressure, of pulse pressure, and inversely of heart rate, wherein the measurement system is preferentially configured to provide the noninvasive systolic arterial pressure SAPni, the noninvasive mean arterial pressure MAPni and the noninvasive diastolic arterial pressure DAPni. The measurements are preferentially executed with short breaks with an unpressurized cuff between consecutive measurements to allow venous return. These short breaks are preferentially within a range from 5 to 10 s. During the measurement arterial perfusion of the part encased by the shell like an upper arm or a wrist of a subject is preferentially never completely interrupted, because clamping pressure preferentially permanently stays below SAP. The measurement is therefore less stressful to the subject compared to conventional oscillometric measurements.

The traditional oscillometric noninvasive blood pressure measurement method uses a continuous deflation or a step-deflation method to determine the blood pressure. A blood pressure cuff is inflated to a target clamping pressure above SAP and then deflation is performed continuously or step-wise. In a traditional device it might be determined whether actual SAP has been exceeded by slowly deflating and if it is found deflation has not been started well above or at or below SAP according to a proprietary algorithm, deflation is stopped and it is inflated to a higher target pressure well above SAP and then it is deflated again.

The company Nihon Kohden uses a noninvasive blood pressure measurement called iNIBP. This blood pressure measurement uses an algorithm which detects pressure oscillations to determine blood pressure during the inflation of a blood pressure cuff. The measurement is completed after detecting SAP with clamping pressure having exceeded SAP. If the blood pressure cannot be determined during inflation, a step-deflation is performed after inflation.

However, the article "Validation of inflationary noninvasive blood pressure monitoring in the emergency room" by J. Sasaki et al., Blood Pressure Monitoring, pages 325-329 (2015) discloses that in emergency rooms the iNIBP blood pressure measurement often needs the step-deflation after the inflation. In particular, in more than 30 percent of the investigated cases a step-deflation was needed in addition to the inflation. The measurement time can become therefore relatively long. Moreover, increasing clamping pressure to high levels above SAP can cause discomfort and/or pain to an awake subject. In contrast to this, the measurement system 1 described above with reference to, for instance, FIG. 1 provides a reliable method for a fast determination of blood pressure with clamping pressures not exceeding SAP. Due to a relatively short measurement time and a relatively low maximal cuff pressure, this blood pressure measurement is very convenient for the individual and the likelihood of potential complications such as thrombophlebitis, pain, ecchymosis, limp edema, peripheral neuropathy, et cetera can be reduced.

In an embodiment TPlow can be at DAP or higher. TPlow defines the tissue pressure at the beginning of the measurement time period, i.e. at the beginning of the slow inflation period, wherein the slow inflation may be terminated when a certain end criterion is reached. End criteria have been described above.

Although in above described embodiments the features are determined by using the TPac pulses, the features can also be determined by using directly the measured pressure pulses, i.e. the TP pulses. It is also possible to process the TP pulses in another way, i.e. not by subtracting the mean TP value for determining the TPac pulses. For instance, for the respective measured pressure pulse the pressure values at t.start and t.stop can be connected by a straight line and this straight line can be subtracted from the respective measured pressure pulse, in order to determine a features determination pulse.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Calculations like the determination of an end measurement time point, of features of pulses, of certain curves, of blood pressure values, et cetera performed by one or several units or devices can be performed by any other number of units or devices. The calculations and determinations and/or the control of the measurement systems in accordance with the control method can be implemented as program code means of a computer and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope. In particular, the letters like TPP, TPA, et cetera used in brackets in the claims as reference signs should not be construed as limiting the scope. For instance, also other features than the features, which are represented by the reference signs, can be used in accordance with the claims.

The invention relates to a control device for controlling a blood pressure measurement system. An applicator applies increasing pressure to a subject's part in a measurement time period, while the pressure on the skin of the subject's part, which comprises a plurality of pressure pulses, is measured. For each pressure pulse of at least some of the plurality of pressure pulses, several features, which characterize the respective pressure pulse, are determined, wherein an end measurement time point, at or after which the measurement time period is to be stopped, is determined based on these features, and wherein, when or after the end measurement time point has been reached, i.e. when the measurement time period is to be stopped, the applied pressure is decreased to start the following post-blood-pressure-measurement time period. This allows for a reduced blood pressure measurement time and maximum tissue pressure exerted on the skin.

The invention claimed is:

1. A control device for controlling a measurement system for measuring blood pressure of a subject, wherein the measurement system comprises a) a shell configured to encase a part of the subject, through which blood flows, b) a pressure applicator configured to apply, from outside the shell, pressure to the shell and thereby to the encased part of the subject, and c) a pressure sensor configured to measure the pressure (TP) on the skin of the encased part of the subject, wherein the control device is configured to control the measurement system such that:

the pressure applicator increases the applied pressure in a measurement time period and decreases the applied pressure in a following post-blood-pressure-measurement time period, the pressure sensor measures the pressure on the skin at least during the measurement time period, wherein the measured pressure (TP) comprises a plurality of pressure pulses, wherein the control device is configured to determine, for each pressure pulse of at least some of the plurality of pressure pulses, several features comprising at least:

(i) a duration of a respective features determination pulse (t(pulse));

(ii) an area of the respective features determination pulse (TPA/TPA.norm);

(iii) a difference (TPP) between a features determination pulse's maximum systolic pressure (TPsys) and a features determination pulse's pressure at the end-diastolic point (TPdia); and (iv) a width at half maximum (W50) of the respective features determination pulse, which characterize the respective pressure pulse, to determine an end measurement time point, at or after which the measurement time period is to be stopped, based on the features TPP, t(Pulse), TPA/TPA.norm, and W50 determined for the at least some of the plurality of pressure pulses, and to control the pressure applicator such that, when or after the end measurement time point has been reached, said pressure applicator decreases the applied pressure to start the following post-blood-pressure-measurement time period;

wherein the control device is configured to, in order to determine for a respective pressure pulse several features, provide a features determination pulse based on the respective pressure pulse, and determine at least two of the following features:

(i) the difference (TPP) between the features determination pulse's maximum systolic pressure (TPsys) and the features determination pulse's pressure at the end-diastolic point (TPdia);

(ii) the duration (t(pulse)) of the respective features determination pulse;

(iii) the area (TPA/TPA.norm) of the respective features determination pulse; and (iv) the width at half maximum (W50) of the respective features determination pulse; and wherein the control device is configured to determine an end determination combination value (TPWP_E) for a respective pressure pulse based on at least one of the following calculations:

(1) multiplying a) the area (TPA/TPA.norm) to the power of a predetermined first exponent (exp1) with b) the difference (TPP) to the power of a predetermined second exponent (exp2);

(2) dividing a) the area (TPA/TPA.norm) to the power of a predetermined third exponent (exp3) by b) the duration (t(pulse)) to the power of a predetermined fourth exponent (exp4) to produce a first resulting quotient; and multiplying the first resulting quotient with c) the difference (TPP) to the power of a predetermined fifth exponent (exp5).

2. The control device as defined by claim 1, wherein the control device is configured to determine:

for a respective pressure pulse, an end determination combination value (TPWP_E) by combining at least two of the features (TPP, t(Pulse), TPA/TPA.norm, W50), which have been determined for the respective pressure pulse, such that for several pressure pulses, which are present at different times, several end determination combination values (TPWP_E) are determined, wherein the several end determination combination values (TPWP_E) determined for the several pressure pulses and hence for the several times form an end determination curve (TPWP_E-curve), and the end measurement time point based on the formed end determination curve (TPWP_E-curve).

3. The control device as defined by claim 1, wherein the control device is configured to determine an end determination combination value (TPWP_E) for a respective pressure pulse based on a further multiplication with the width at half maximum to the power of a further predetermined exponent.

4. The control device as defined by claim 1, wherein the control device is configured to determine:

for a respective pressure pulse a blood pressure determination combination value (TPWP_M) by combining at least two of the determined features (TPP, t(Pulse), TPA/TPA.norm, W50) such that for several pressure pulses, which are present at different times, several blood pressure determination combination values (TPWP_M) are determined, wherein the several blood pressure determination combination values (TPWP_M) determined for the several pressure pulses and hence for several times form a blood pressure determination curve (TPWP_M-curve), the blood pressure based on the blood pressure determination curve (TPWP_M-curve).

5. The control device as defined by claim 4, wherein the control device is configured to determine a maximum of the blood pressure determination curve (TPWP_M-curve) and to determine the blood pressure based on the determined maximum and the measured pressure (TP).

6. The control device as defined by claim 4, wherein the control device is configured to determine a blood pressure determination combination value (TPWP_M) for a respective pressure pulse based on at least one of the following calculations:

multiplying a) the determined area (TPA/TPA.norm) to the power of a predetermined tenth exponent (exp10) with b) the determined difference (TPP) to the power of a predetermined eleventh exponent (exp 11), dividing a) the determined area (TPA/TPA.norm) to the power of a predetermined twelfth exponent (exp12) by b) the determined duration (t(pulse)) to the power of a predetermined thirteenth exponent (exp13) so as to produce a second resulting quotient and multiplying the second resulting quotient with c) the determined difference (TPP) to the power of a predetermined fourteenth exponent (exp14).

7. The control device as defined by claim 6, wherein the control device is configured to determine a blood pressure determination combination value (TPWP_M) for a respective pressure pulse based on a further multiplication with the width at half maximum (W50) to the power of a further predetermined exponent.

8. The control device as defined by claim 5, wherein the control device is configured to determine the end determination curve (TPWP_E-curve) such that it fulfills one of the following conditions:

a maximum of the end determination curve (TPWP_E-curve) occurs temporally before a maximum of the blood pressure determination curve (TPWP_M-curve), a maximum of the end determination curve (TPWP_E-curve) occurs temporally at or after a maximum of the blood pressure determination curve (TPWP_M-curve) and the decrease of the end determination curve (TPWP_E-curve) after its maximum is steeper than the decrease of the blood pressure determination curve (TPWP_M-curve) after its maximum, and the end determination curve (TPWPE-curve) is identical to the blood pressure determination curve (TPWP_M-curve).

9. The control device as defined by claim 2, wherein the control device is configured to determine:

for a respective pressure pulse a blood pressure determination combination value (TPWP_M) by combining at least two of the determined features (TPP, t(Pulse), TPA/TPA.norm, W50) such that for several pressure pulses, which are present at different times, several blood pressure determination combination values (TPWP_M) are determined, wherein the several blood pressure determination combination values (TP WP M) determined for the several pressure pulses and hence for several times form a blood pressure determination curve (TPWP_M-curve), the blood pressure based on the blood pressure determination curve (TPWP_M-curve), and the end measurement time point further based on the blood pressure determination curve (TPWP_M-curve).

10. The control device as defined by claim 9, wherein the control device is configured to determine the end measurement time point by determining when a) the end determination curve (TPWP_E-curve) has fallen, after having passed its maximum, to a value being equal to or smaller than a predefined percentage of the maximum and b) the blood pressure determination curve (TPWP_M-curve) has reached or passed its maximum.

11. The control device as defined by claim 10, wherein the predefined percentage of the maximum is within a range from 40 percent to 95 percent.

12. The control device as defined by claim 1, wherein the control device is configured to control the pressure applicator such that it increases the applied pressure with a first rate in a pre-measurement time period which is followed by the measurement time period in which the applied pressure is increased with a second rate, wherein the first rate is larger than the second rate.

13. The control device as defined by claim 12, wherein the control device is configured to control the pressure applicator such that at the end of the pre-measurement time period the measured pressure (TP) is within the range of 15 to 30 mmHg.

14. The control device as defined by claim 12, wherein the control device is configured to:
   store or receive a previous diastolic arterial pressure (DAPprev) obtained by a previous blood pressure measurement,
   determine a first end measured pressure (TPlow), which should be present at the end of the pre-measurement time period, depending on the previous diastolic arterial pressure (DAPprev) such that the first end measured pressure (TPlow) is smaller than the previous diastolic arterial pressure (DAPprev),
   control the pressure applicator such that the measured pressure (TP) at the end of the pre-measurement time period is equal to or smaller than the determined first end measured pressure (TPlow).

15. The control device as defined in claim 14, wherein the control device is configured to determine the first end measured pressure (TPlow) such that it is 90 percent or less of the previous diastolic arterial pressure (DAPprev).

16. The control device as defined by claim 14, wherein the control device is configured to further store or receive the time at which the previous diastolic arterial pressure (DAPprev) had been measured and to determine the first end measured pressure (TPlow) depending on i) the previous diastolic arterial pressure (DAPprev) and ii) a temporal distance to the blood pressure measurement, at which the previous diastolic arterial pressure (DAPprev) had been measured, as indicated by the stored time.

17. The control device as defined by claim 12, wherein the control device is configured to:
   store or receive a previous pressure measured by the pressure sensor in a time period in between an end of a previous measurement time period of a previous blood pressure measurement and a start of the pre-measurement time,
   control the pressure applicator such that the measured pressure (TP) at the start of the pre-measurement time period is equal to or smaller than a predefined pressure value based on the stored or received previous measure.

18. A measurement system for measuring blood pressure of a subject, wherein the measurement system comprises:
   a shell configured to encase a part of the subject, through which blood flows,
   a pressure applicator configured to apply, from outside the shell, pressure to the shell and thereby to the encased part of the subject,
   a pressure sensor configured to measure the pressure (TP) on the skin of the encased part of the subject, and
   a control device as defined in claim 1.

19. A control method for controlling a measurement system as defined by claim 18, wherein the control method includes:
   increasing the applied pressure in a measurement time period and decreasing the applied pressure in a following post-blood-pressure-measurement time period by using the pressure applicator,
   measuring the pressure (TP) on the skin at least during the measurement time period by using the pressure sensor, wherein the measured pressure (TP) comprises a plurality of pressure pulses, wherein, for each pressure pulse of at least some of the plurality of pressure pulses, several features (TPP, t(Pulse), TPA, TPA.norm, W50), which characterize the respective pressure pulse are determined and wherein an end measurement time point, at or after which the measurement time period is to be stopped, is determined based on the features (TPP, t(Pulse), TPA/TPA.norm, W50) determined for the at least some of the plurality of pressure pulses, and wherein the pressure applicator is controlled such that, when or after the end measurement time point has been reached, it decreases the applied pressure to start the following post-blood-pressure-measurement time period.

20. A computer program for controlling a measurement system, the computer program comprising non-transitory program code means for causing the measurement system to carry out the steps of claim 19, when the computer program is run on the control device of the measurement system.

* * * * *